(12) United States Patent
Tohyama et al.

(10) Patent No.: US 7,364,847 B2
(45) Date of Patent: Apr. 29, 2008

(54) NUCLEIC ACID PARTICIPATING IN THE FORMATION OF PRESENILIN-2-GENE EXON 5-DEFECTIVE SPLICING VARIANT

(75) Inventors: Masaya Tohyama, Toyonaka (JP); Taiichi Katayama, Ikeda (JP); Takayuki Manabe, Ibaraki (JP); Kazunori Imaizumi, Ikoma (JP); Yoko Ikeda, Tokyo (JP)

(73) Assignee: Japan Science and Tehcnology Agency, Saitama (JP)

( * ) Notice: Subject to any disclaimer, the term of this patent is extended or adjusted under 35 U.S.C. 154(b) by 221 days.

(21) Appl. No.: 10/482,115

(22) PCT Filed: Jun. 27, 2002

(86) PCT No.: PCT/JP02/06462

§ 371 (c)(1),
(2), (4) Date: Dec. 24, 2003

(87) PCT Pub. No.: WO03/002742

PCT Pub. Date: Jan. 9, 2003

(65) Prior Publication Data

US 2004/0267004 A1    Dec. 30, 2004

(30) Foreign Application Priority Data

Jun. 27, 2001    (JP)    ............ 2001-195472

(51) Int. Cl.
*C12Q 1/68* (2006.01)
*G01N 33/53* (2006.01)
*C07H 21/00* (2006.01)

(52) U.S. Cl. ............ 435/6; 435/7.1; 536/24.1
(58) Field of Classification Search ............ 536/24.1
See application file for complete search history.

(56) References Cited

U.S. PATENT DOCUMENTS 6,020,143 A * 2/2000 St. George-Hyslop et al. ............ 435/7.1

FOREIGN PATENT DOCUMENTS

WO    WO 97/03192    * 1/1997
WO    WO 99/16874 A1    4/1999
WO    WO 99/60122 A1    11/1999

OTHER PUBLICATIONS

Ji Y-S et al. Hypoxia induces high-mobility-group protein I(Y) and transcription of the cyclooxygenase-2 gene in human vascular endothelium. Circulation Research, 1998; 83: 295-304.*
Takami K et al. Expression of presenilin-1 and -2 mRNAs in rat and Alzheimer's disease brains. Brain Res, 1997; 748(1-2): 122-130.*
Prihar G et al. Structure and alternative splicing of the Presenilin-2 gene. NeuroReport, 1996; 7: 1680-1684.*
Sato et al., J. Biol. Chem., vol. 276, No. 3, pp. 2108-2114 (2001).
Sato et al., J. Neurochem., vol. 72, No. 6, pp. 2498-2505 (1999).
D. J. Selkoe et al., Annu. Rev. Neurosci., 17, 489-517 (1994).
Neto et al., PNAS, vol. 97, No. 7, pp. 3491-3496 (2000).
Genebank (2004) Accession No. CV411805.
Levy-Lahad et al., Genebank (1997) Accession No. U50871.
Levy-Lahad et al., Genomics, vol. 34, No. 2, pp. 198-204 (1996).
Manabe et al., Cell Death and Differentiation, vol. 10, No. 6, pp. 698-708 (2003).
Katayama, et al., Japanese Journal of Clinical Medicine, vol. 61, No. 4, pp. 677-688 (2003).
Manabe et al., Neuroscience Letters, vol. 328, No. 2, pp. 198-200 (2002).
Katayama et al., Journal of Chemical Neuroanatomy, vol. 28, Nos. 1-2, pp. 67-78 (2004).
Eckner et al., Nucleic Acids Research, vol. 17, No. 15, pp. 5947-5959 (1989).
Sato et al., Society for Neuroscience Abstracts, vol. 25, No. 1-2, pp. 55 (1999).
Manabe et al., Society for Neuroscience Abstracts, vol. 27, No. 1, pp. 1440 (2001).

* cited by examiner

*Primary Examiner*—Jeffrey Stucker
*Assistant Examiner*—Stephen Gucker
(74) *Attorney, Agent, or Firm*—Birch, Stewart, Kolasch & Birch, LLP

(57) ABSTRACT

The present invention provides a means for treatment and/or prevention of a disease caused by aberrant splicing, a neurodegenerative disease represented by Alzheimer's disease, or the like. The present invention relates to a nucleic acid which can be associated with generation of a splice variant that lacks exon 5 of presenilin-2 gene, an inhibitor for inhibiting a binding between protein-nucleic acid caused by aberrant splicing, and a method for screening the inhibitor.

5 Claims, 24 Drawing Sheets

Fig. 2
Hippocampal CA1 Region
Control Brain
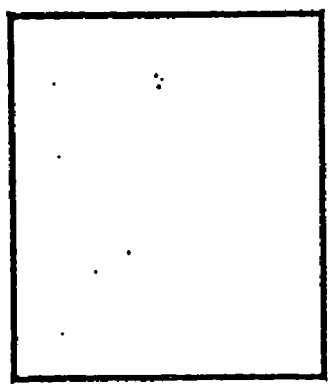
sAD Brain

Silver Staining

Fraction with Binding Activity

Binding Assay

Fraction with Binding Activity

N: Normoxia
H: Hypoxia
Ab: Anti-HMGI/Y Antibody

5'
UGGUGGUGCUCUACAAGU

ACCGCUGCUACAAGgugagg cccuggcccugcccuccagccacgcu ucucuccg
3'

Fig. 19
Immunoprecipitation (AbH)
Western (AbU)
SK-N-SH Cell
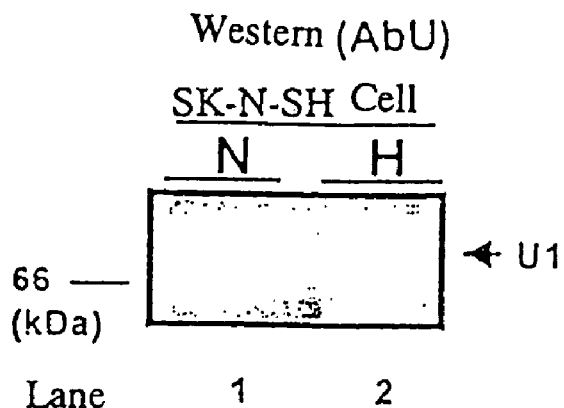
Immunoprecipitation (AbU)
Western (AbH)
SK-N-SH Cell
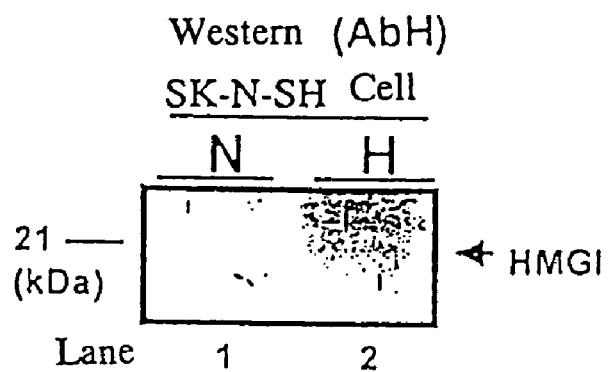
N: Normoxia
H: Hypoxia
AbU: Anti-U1 snRNP Antibody
AbH: Anti-HMGI/Y Antibody Fig. 22
| Hippocampal CA1 Region ||
|---|---|
| Normal Brain | Sporadic sAD Brain |
| 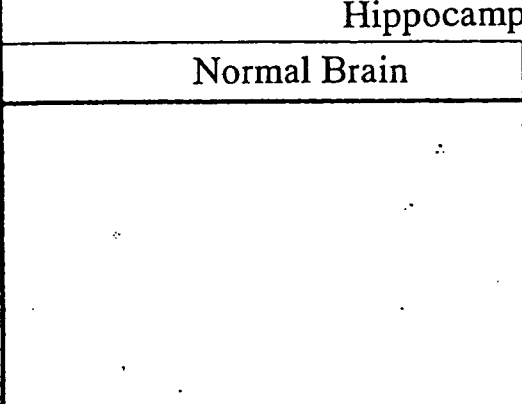 | 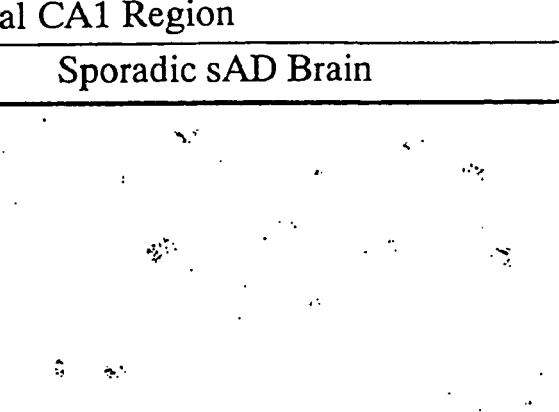 |

Fig. 23

No. 1, 5'-TCTGGATCCTGCCTTCTCCCTCAGCATCTACACGACATTCACTGAGGACACGAATTCAGA-3'/3'-AGACCTAGGACGGAAGAGGGAGTCGTAGATGTGCTGTAAGTGACTCCTGTGCTTAAGTCT-5'; No. 2, 5'-TCTGGATCCTGAGGACACACCCTCGGTGGGCCAGCGCCTCCTCAACTCCGTGAATTCAGA-3'/3'-AGACCTAGGACTCCTGTGTGGGAGCCACCCGGTCGCGGAGGAGTTGAGGCACTTAAGTCT-5'; No. 3, 5'-TCTGGATCCCAACTCCGTGCTGAACACCCTCATCATGATCAGCGTCATCGTGAATTCAGA-3'/3'-AGACCTAGGGTTGAGGCACGACTTGTGGGAGTAGTACTAGTCGCAGTAGCACTTAAGTCT-5'; No. 4, 5'-CTCGGATCCTGATCAGCGTCATCGTGGTTATGACCATCTTCTTGGTGGTGCGAATTCGAG-3'/3'-GAGCCTAGGACTAGTCGCAGTAGCACCAATACTGGTAGAAGAACCACCACGCTTAAGCTC-5'; No. 5, 5'-TCTGGATCCTGGTGGTGCTCTACAAGTACCGCTGCTACAAGGTGAGGCCCTGAATTCAGA-3'/3'-AGACCTAGGACCACCACGAGATGTTCATGGCGACGATGTTCCACTCCGGACTTAAGTCT-5'; No. 6, 5'-GATCCGACCATCTTCTTGGTGGTG-3'/3'-GGCTGGTAGAAGAACCACCACTTAA-5'; No. 7, 5'-GATCCGCTCTACAAGGCTGCTACAAGG-3'/3'-GGCGAGATGTTCCGACGATGTTCCTTAA-5'; No. 8, 5'-GATCCGCTCTAAAAGTACCGCTGCTAAAAGG-3'/3'-GGCG ACATTTTCATGGCGACGATGTTCC-5'; No. 9, 5'-TCTGGATCCTGGTGGTGCTCTACAA GTAGAATTCAGA-3'/3'-AGACCTAGGACCACCACGAGATGTTCATCTTAAGTCT-5'; No. 10, 5' TCTGGATCCGCTCTACAAGTACCGCTGCTACAAGGAATTCAGA-3'/3'-AGACCTAGGCGAGATGTTCATGGCGACGATGTTCCTTAAGTCT-5'; No. 11, 5'-TCTGGATCCC CGCTGCTACAAGGTGAGGCCCTGAATTCAGA-3'/3'-AGACCTAGGGGCGACGATGTTCCACTCCGGACTTAAGTCT-5'

GGTTCATTCTGCGGTAT  G  G  T  A  T  C  T  G
                              ATC  T  G  T  A  A  T  T  C  CATGGTGGCTACTGGAACTA
                     GTGGAGGCTGCCGCG  A  G  T  T  A  T  C  A  CAGTATAG
                            ACCTA  G  G  T  T  A  T  T  C  TGCGGTATGGTTATCTG
                GGGTGCCTAGCTCCGGAACAT  G  G  T  T  A  T  T  G  A
                 CGTTCTCTTTCGGAAAC  G  G  T  T  T  T  G  AGCACG
                TGAGGCATGAAGGTAATTACT  G  C  A  T  A  T  T  G  A
                      GGCCGCGTGT  A  G  A  T  A  T  T  G  GGATTTGGTGTG
                        CGTTCTCTTTC  G  G  A  A  A  T  T  T  TTGAGCACG
                           TGACCA        A  G  T  A  A  A  T  C  C GTCCCTCACTAGTGAA
                        GCCATGTTTTA  G  A  T  A  A  T  T  G  TGCTTAGGCGT
                       TCTGAGGCATGAA  G  G  T  A  A  T  T  A  CTGCATCATT
                          TATCCAGTG  G  A  T  A  A  T  T  C  CCCAATGTTATCT
               CGTTCCGACCAATGGGTTCG  G  A  T  A  A  T  A  C  GTT
                              CTTCTGC  G  G  T  A  T  A  A  G  GTGGGTTGGTGTGCTC
                GAGGTGTCAGGCGACACCT  A  A  A  A  A  T  T  C  ACGC
                      ATATCCTGCC  A  A  A  A  A  T  T  T  GTTCTCGGGGCTGA
                       TGTTTCGCGTA  A  A  G  T  A  T  T  A  CGTTGCTCTTTT
                 GTCGGGCCTGTATTTTGGT  T  G  C  T  A  T  T  T  TGAA
                     GCGAGTCGGGCC  C  T  G  T  A  T  T  T  TGGTTGCTATTT
                     TTGAATTAGGGTGC  T  A  T  A  T  T  T  TGCATTTTGA
                 GTCGGGCCTGTATTTTGGTT  G  C  T  A  T  T  T  T  GAA
                     GCGAGTCGGGCC  T  G  T  A  T  T  T  T  GGTTGCTATTT
                 CCACTTTGAATTAGGGTGCT  A  T  A  T  T  T  T  T  GCAT
                               GTGG  A  T  A  A  A  T  T  C  CCCAATGTTATCTTATGAA
                  CTTTGAATTAGGGTGCT  A  T  A  T  T  T  T  T  GCATTT
            CGTGTTTCGCCAGAACCGCACTAG  A  G  C  A  A  T  T  T  GAA
                       CTTTGAATTAGGG  T  G  C  T  A  T  A  T  GGTTTGCATTTT
                                  GT  G  G  A  T  A  A  A  T  TCCCCAATGTTATCTTATGAA
                 GGTGCCGATACGTAACTCAC  C  G  C  A  T  T  C  T  TGG
                 CGTTCCGACCAATGGGTTC  G  A  T  A  A  T  A  CGTT
                GGTGCCGATACGTAACTCACC  G  C  A  T  T  T  T  G  GC
                            GGTGCCGATA  C  G  T  A  A  T  C  A  CCGCATTCTTGGC
                              CACT  T  T  G  A  A  T  T  A  GGGTGCTATATGTTTTGCA
                TTGAATTAGGGTGCTATATGTT  T  T  G  C  A  T  T  T  T
                 CGTTCTCTTTCGGAAAC  G  G  T  T  T  T  T  T  G  AGCACG
                AGGTTCGTGCACCCGGACCAC  A  G  T  T  T  T  T  T  CA
```

Fig. 25
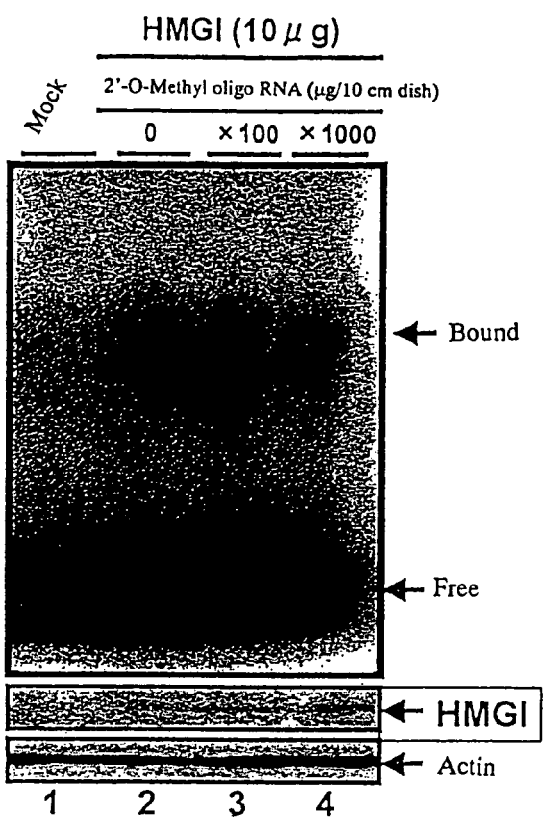
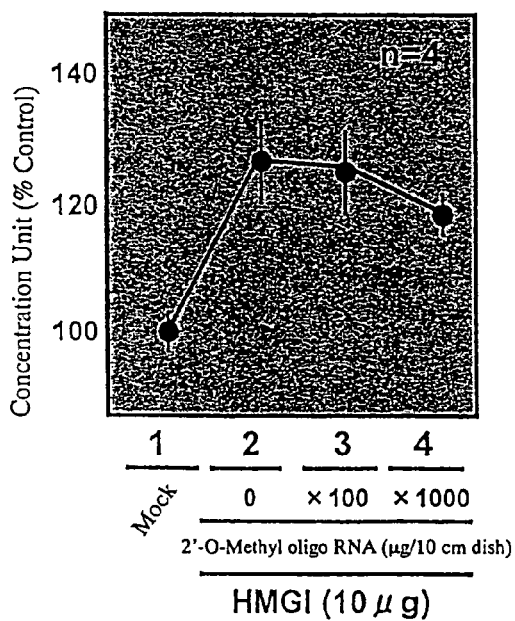

NUCLEIC ACID PARTICIPATING IN THE FORMATION OF PRESENILIN-2-GENE EXON 5-DEFECTIVE SPLICING VARIANT

TECHNICAL FIELD

The present invention relates to a nucleic acid which can be a target for treatment and/or prevention of a disease caused by aberrant splicing, a neurodegenerative disease represented by Alzheimer's disease, or the like, an inhibitor for inhibiting a binding between protein-nucleic acid caused by aberrant splicing, and a method for screening the inhibitor.

BACKGROUND ART

Alzheimer's disease (AD) is a neurodegenerative disease, and the diseases of over 90% of the AD patients are classified as sporadic Alzheimer's disease (sAD). Further, the AD patients show clinical features such as progressive loss of memory and other cognitive abilities. Pathologically, neuronal loss, glial proliferation, accumulations in the brain of intraneuronal neurofibrillary tangles and extracellular deposition of senile plaques primarily composed of β-amyloid protein (Aβ), are found in the AD brain [Selkoe, D. J. et al., *Annu. Rev. Neurosci.*, 17, 489-517 (1994)]. Further, as other pathological characteristics, it has been known that an aberrant protein (PS2V) encoded by a variant of presenilin-2 gene is found in apoptotic pyramidal cells of each of cerebral cortex and hippocampal CA1 region of the sAD brain by immunohistochemical analysis [Sato, N. et al., *J. Biol. Chem.*, 276, 2108-2114 (2001)].

PS2V has been known to be induced by hypoxic stimulation in cultured human neuroblastoma SK-N-SH cells [Sato, N. et al., *J. Neurochem.*, 72, 2498-2505 (1999)]. Further, this hypoxia-induced PS2V is shown be dependent on a new protein synthesis in each of oxidative stress and SK-N-SH cells by using an antioxidant and cycloheximide [Sato et al. mentioned above, (1999)].

It has been known that a glucose-regulated protein (GRP78), which is endoplasmic reticulum (ER) stress-responsive molecular chaperone, is reduced by the above PS2V, and the production of β-amyloid protein is increased in PS2V-expressed cells [Sato, N. et al., *J. Biol. Chem.*, 276, 2108-2114 (2001)].

However, although the possibility that PS2V is one of important factors for neuronal death has been suggested, the details of the mechanisms of the generation of PS2V and incidence of the disease have not been sufficiently known in the present situation.

DISCLOSURE OF INVENTION

An object of the present invention is to provide a nucleic acid capable of achieving at least one of providing a factor relating to the generation of a splice variant that lacks exon 5 of presenilin-2 gene found in sporadic Alzheimer's disease and its information, providing a region in which the factor and presenilin-2 gene are associated to bind thereto and its information, and providing a target for a treatment and/or prevention of a disease caused by aberrant splicing based on an inhibitory mechanism of the factor or the binding, namely a nucleic acid which can be associated with the generation of a splice variant that lacks exon 5 of presenilin-2 gene. Another object of the present invention is to provide a method for screening an inhibitor for inhibiting binding between the factor and presenilin-2 gene, capable of providing a compound capable of treating and/or preventing a disease caused by aberrant splicing on the basis of the inhibitory mechanism of the above factor or the above binding. A further object of the present invention is to provide an inhibitor for inhibiting binding between exon 5 of presenilin-2 gene and HMG-I protein, capable of inhibiting generation of a splice variant that lacks exon 5 of presenilin-2 gene, and treating and/or preventing a disease which can be caused by aberrant splicing.

Concretely, the present invention relates to:

[1] a nucleic acid capable of binding to HMG-I protein, wherein the nucleic acid causes presenilin-2 gene exon 5-lacked type aberrant splicing by the association with the HMG-I protein;

[2] a nucleic acid capable of binding to HMG-I protein, wherein the nucleic acid is a part of a presenilin-2 mRNA precursor;

[3] a nucleic acid capable of binding to HMG-I protein, comprising the nucleotide sequence shown in SEQ ID NO: 1 and/or the nucleotide sequence shown in SEQ ID NO: 2;

[4] the nucleic acid according to the above [3], capable of binding to the HMG-I protein, wherein the nucleic acid comprises at least one nucleotide sequence selected from the group consisting of SEQ ID NO: 3, 4, 5, 6 and 7;

[5] the nucleic acid according to the above [3] or [4], wherein the nucleic acid has 10 to 100 bases in length;

[6] an antisense molecule of the nucleic acid according to any one of the above [1] to [5];

[7] a method for screening an inhibitor for binding between exon 5 of presenilin-2 gene and HMG-I protein, characterized by detecting in the presence or absence of a substance to be tested a binding between HMG-I protein and ① a nucleic acid capable of binding to HMG-I protein, wherein the nucleic acid causes presenilin-2 gene exon 5-lacked type aberrant splicing by the association with the HMG-I protein, or ② a nucleic acid capable of binding to HMG-I protein, wherein the nucleic acid is a part of a presenilin-2 mRNA precursor, or determining a binding strength of the binding, wherein the following I) or II):

I) a case where the binding between the nucleic acid and the HMG-I protein is not detected in the presence of the substance to be tested, or II) a case where a binding strength a of binding between the nucleic acid and the HMG-I protein in the presence of the substance to be tested is smaller than a binding strength b of binding between the nucleic acid and the HMG-I protein in the absence of the substance to be tested is used as an index showing that the substance to be tested is an inhibitor for binding between exon 5 of presenilin-2 gene and HMG-I protein;

[8] the screening method according to the above [7], wherein the method comprises the steps of:

(A) contacting

① a nucleic acid capable of binding to HMG-I protein, wherein the nucleic acid causes presenilin-2 gene exon 5-lacked type aberrant splicing by the association with the HMG-I protein, or ② a nucleic acid capable of binding to HMG-I protein, wherein the nucleic acid is a part of a presenilin-2 mRNA precursor, with HMG-I protein in the presence of the substance to be tested; and (B) detecting binding between the nucleic acid and the HMG-I protein;

[9] the screening method according to the above [7], wherein the method comprises the steps of:

(a) contacting

① a nucleic acid capable of binding to HMG-I protein, wherein the nucleic acid causes presenilin-2 gene exon 5-lacked type aberrant splicing by the association with the HMG-I protein, or ② a nucleic acid capable of binding to HMG-I protein, wherein the nucleic acid is a part of a presenilin-2 mRNA precursor, with HMG-I protein under each condition of the presence and absence of the substance to be tested; and (b) determining a binding strength a of binding between the nucleic acid and the HMG-I protein in the presence of a substance to be tested and a binding strength b of binding between the nucleic acid and the HMG-I protein in the absence of a substance to be tested;

[10] the screening method according to any one of the above [7] to [9], wherein the nucleic acid is the nucleic acid of any one of the above [3] to [5];

[11] the screening method according to any one of the above [7] to [10], further comprising the steps of determining binding between a DNA having the nucleotide sequence shown in SEQ ID NO: 66 and the HMG-I protein in the presence of the substance to be tested, and screening a compound not inhibiting the binding; and

[12] an inhibitor for binding between exon 5 of presenilin-2 gene and HMG-I protein, obtainable by a method for screening an inhibitor for binding between exon 5 of presenilin-2 gene and HMG-I protein, characterized by detecting in the presence or absence of a substance to be tested a binding between HMG-I protein and ① a nucleic acid capable of binding to HMG-I protein, wherein the nucleic acid causes presenilin-2 gene exon 5-lacked type aberrant splicing by the association with the HMG-I protein, or ② a nucleic acid capable of binding to HMG-I protein, wherein the nucleic acid is a part of a presenilin-2 mRNA precursor, or determining a binding strength of the binding, wherein the following I) or II):

I) a case where the binding between the nucleic acid and the HMG-I protein is not detected in the presence of the substance to be tested, or II) a case where a binding strength a of binding between the nucleic acid and the HMG-I protein in the presence of the substance to be tested is smaller than a binding strength b of binding of the nucleic acid to the HMG-I protein in the absence of the substance to be tested is used as an index showing that the substance to be tested is an inhibitor for binding between exon 5 of presenilin-2 gene and HMG-I protein;

BRIEF DESCRIPTION OF THE DRAWINGS

FIG. 2 is a diagram showing the results of immunohistochemical detection of PS2V in each of a sAD brain and a control brain. Brain sections for control and sAD of 10 μm in thickness were prepared and thereafter subjected to immunohistochemical detection of PS2V using an anti-SSMAG antibody. These results were obtained by analyzing at least three different kinds of control and AD brains, and the same results were obtained.

In the figure, exon is shown in capital letters, and intron in small letters. Two analogous sequences are shown in bold letters with underlines.

Figure 12:
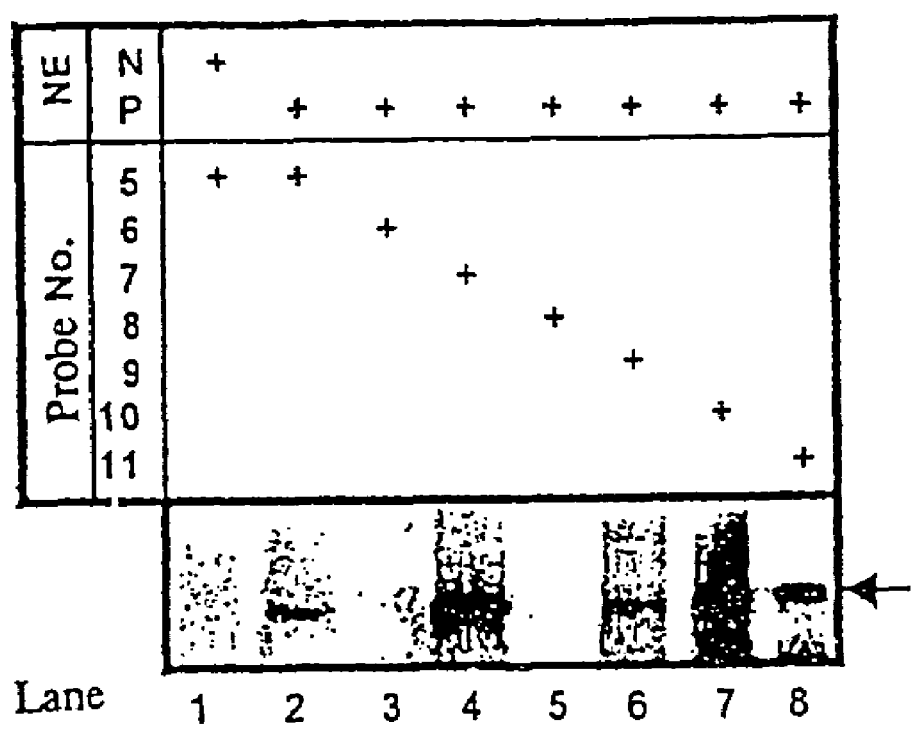

FIG. 12 is a diagram showing the results of examination of a binding site of HMG-I protein in PS2 pre-mRNA. SK-N-SH cells are exposed to normoxia or hypoxia and then collected after 21 hours of stimulation. By the pre-mRNA binding assay using each radioisotope-labeled probe, the nuclear extract from the collected cells is analyzed. Next, the nuclear extract is subjected to SDS-PAGE, followed by exposure to a Bas imaging plate. In the figure, the solid arrow indicates a point of the corresponding molecular weight. These experiments are repeated at least four times using different cell culture media, and the same results are obtained.

Figure 13:
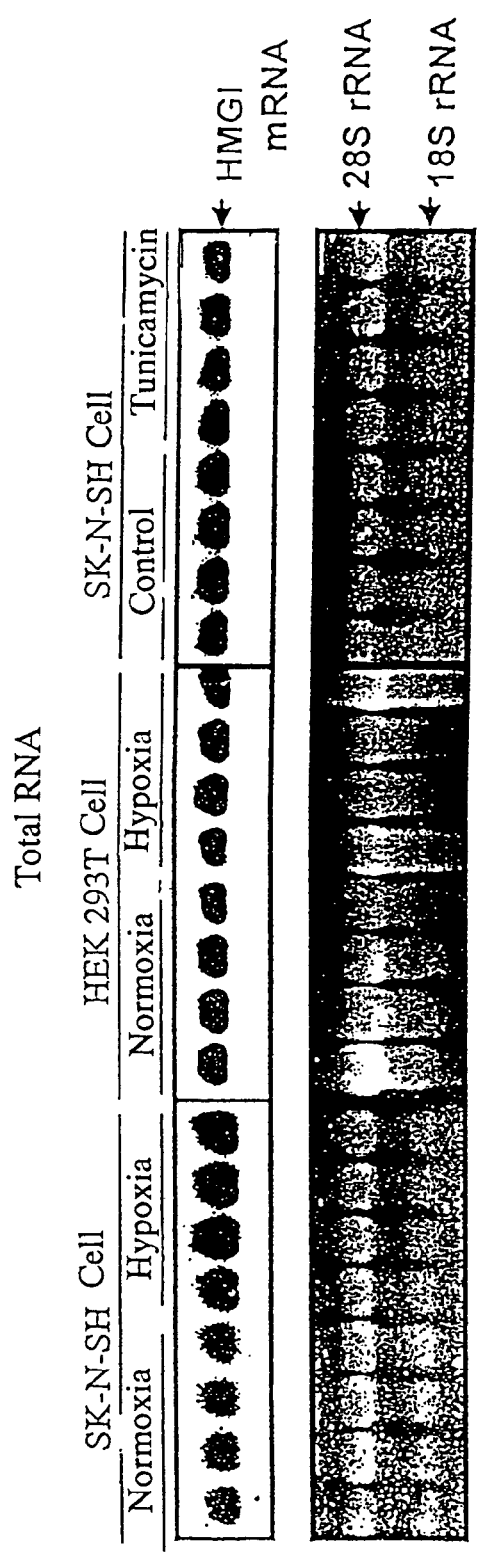

FIG. 13 is a diagram showing the results of examination of the effects of various stresses on expression of HMG-I mRNA (HMGI mRNA in the figure) and the protein corresponding to the mRNA in the cultured cells by Northern blot analysis. The left panel and the central panel each shows the analytical results of the cell lines collected after 21 hours of exposure to normoxia or hypoxia. The right panel shows the analytical results of SK-N-SH cells collected 24 hours after treatment with tunicamycin. The total RNA is electrophoresed on a formaldehyde-formamide gel and subjected to Northern blot assay using a radioisotope-labeled HMG-I cDNA probe. In the figure, a point of the molecular weight is indicated by a solid arrow.

Figure 14:
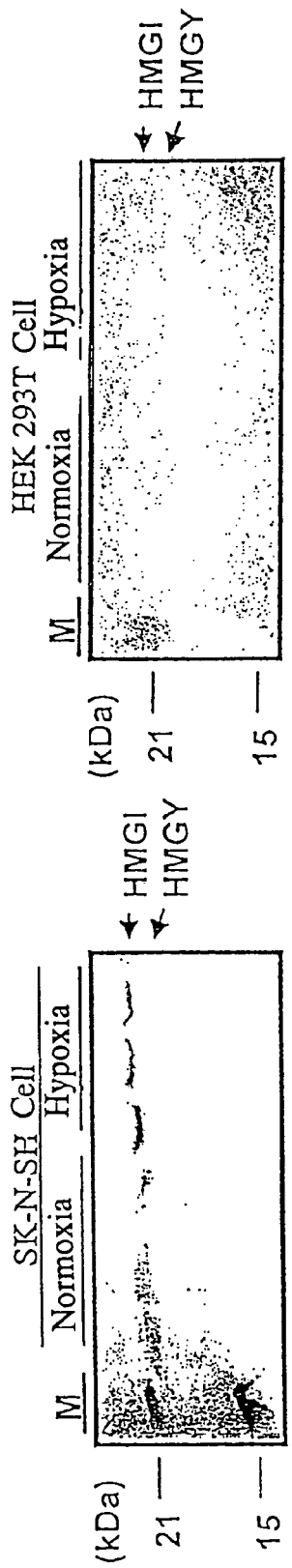

FIG. 14 is a diagram showing the results of examination of the effects of various stresses on expression of HMG-I mRNA and the protein corresponding to the mRNA in the cultured cells by Western blot analysis. Each cell line is exposed to normoxia or hypoxia, and thereafter collected after 21 hours of stimulation. The resulting nuclear extract is subjected to SDS-PAGE and an immunoblot assay using an antibody against with HMG-I/Y protein. In the figure, the solid arrows indicate points of the molecular weights corresponding to the HMG-I (upper panel, "HMGI" in the figure) and HMG-Y (lower panel, "HMGY" in the profile) proteins.

Figure 15:
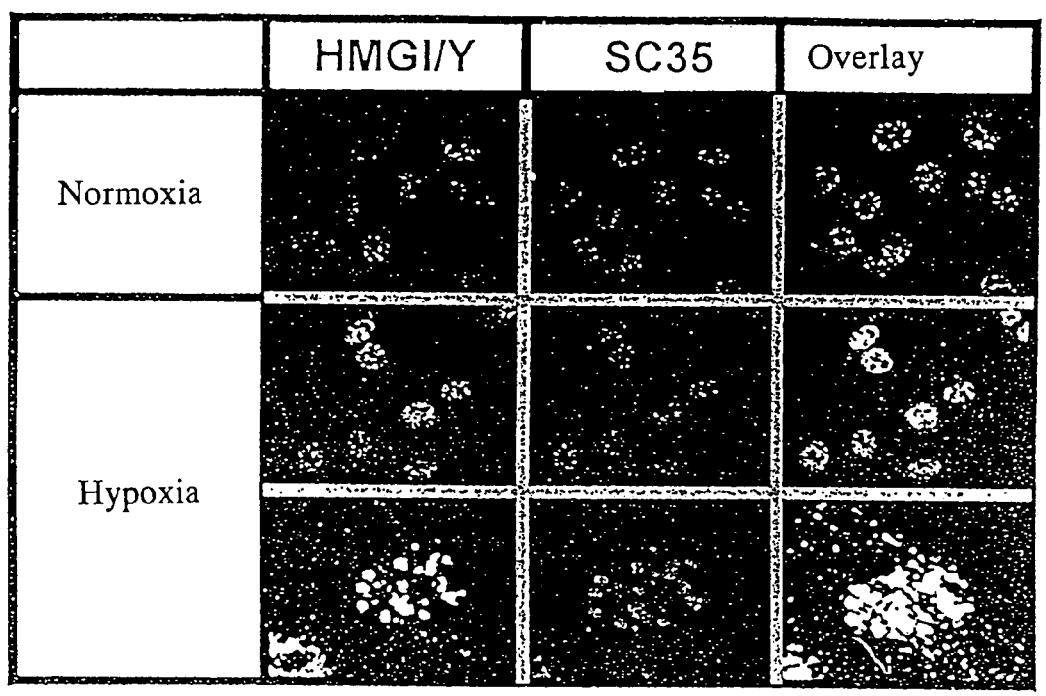

FIG. 15 is a diagram showing the effects of hypoxia on cellular localization of immunoreactive HMG-I protein in SK-N-SH cells. SK-N-SH cells are exposed to normoxia or hypoxia for 21 hours. The cells are immunostained with an anti-HMG-I/Y ("HMGI/Y" in the figure) antibody and anti-SC35 antibody for primary immunoreaction and stained with an FITC-bound secondary antibody and a Cy3-conjugated secondary antibody. These experiments are repeated at least four times using different cell cultures, and the same results are obtained.

Figure 16:
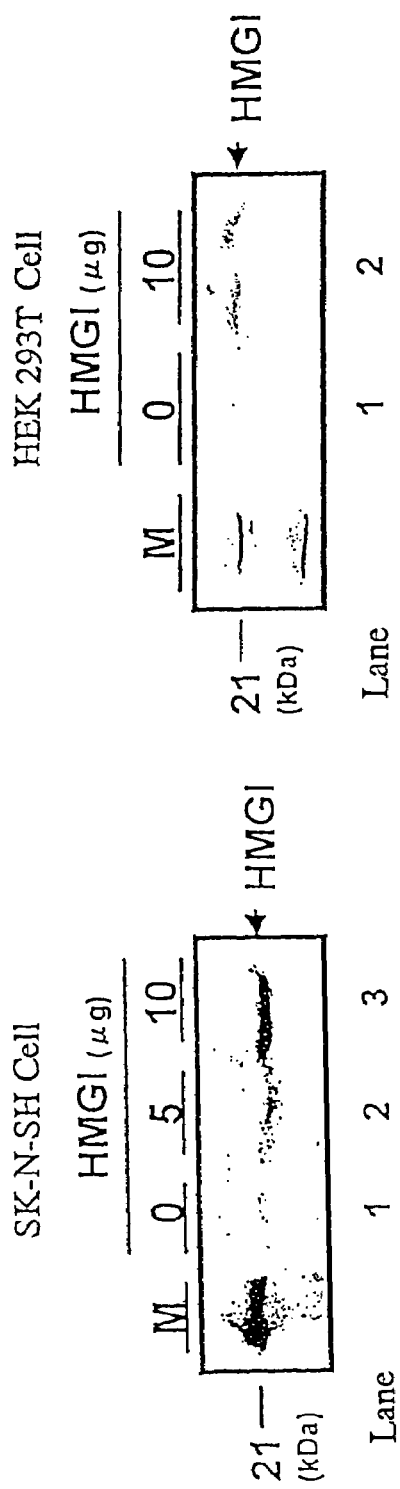

FIG. 16 is a diagram showing the results of examination of the effect of transient expression of HMG-I or HMG-Y on exon 5 skipping in PS2 gene in the cultured cells. Each cell line was transfected with mock or HMG-I, followed by collection 24 hours after the transfection. The nuclear extract was subjected to SDS-PAGE and immunoblot assay using an antibody against HMG-I/Y. The solid arrow indicates a point of the molecular weight corresponding to HMG-I protein ("HMGI" in the figure). These experiments were repeated at least four times using different cell culture media, and the same results were obtained.

Figure 17:
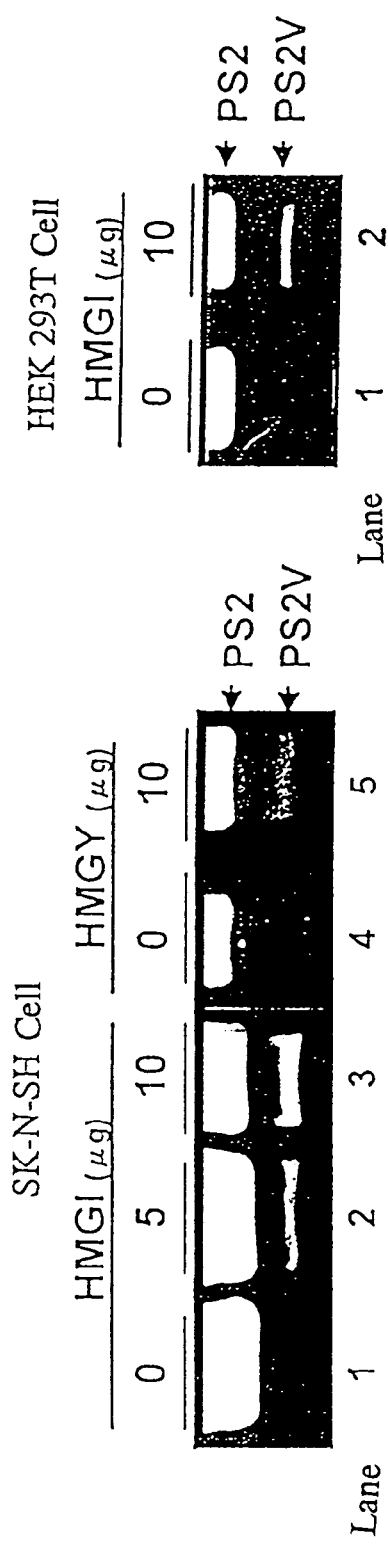

FIG. 17 is a diagram showing the results of examination of the effect of the transient expression of HMG-I or HMG-Y on exon 5 skipping of PS2 gene in the cultured cells. Each cell line was transfected with different amounts of mock, HMG-I ("HMGI" in the figure) or HMG-Y ("HMGY" in the figure), and collected 24 hours after the transfection. The total RNA from the collected cells was subjected to RT-PCR according to a method of a literature [Sato et al., *J. Neurochem.*, 72, 2498-2505 (1999)]. The amplified product was separated on a polyacrylamide gel and visualized by staining with ethidium bromide. The solid arrows indicate points of the molecular weights corresponding to PS2 (upper band) and PS2V (lower part). These experiments were repeated at least 4 times using different cell culture media, and the same results were obtained.

Figure 18:
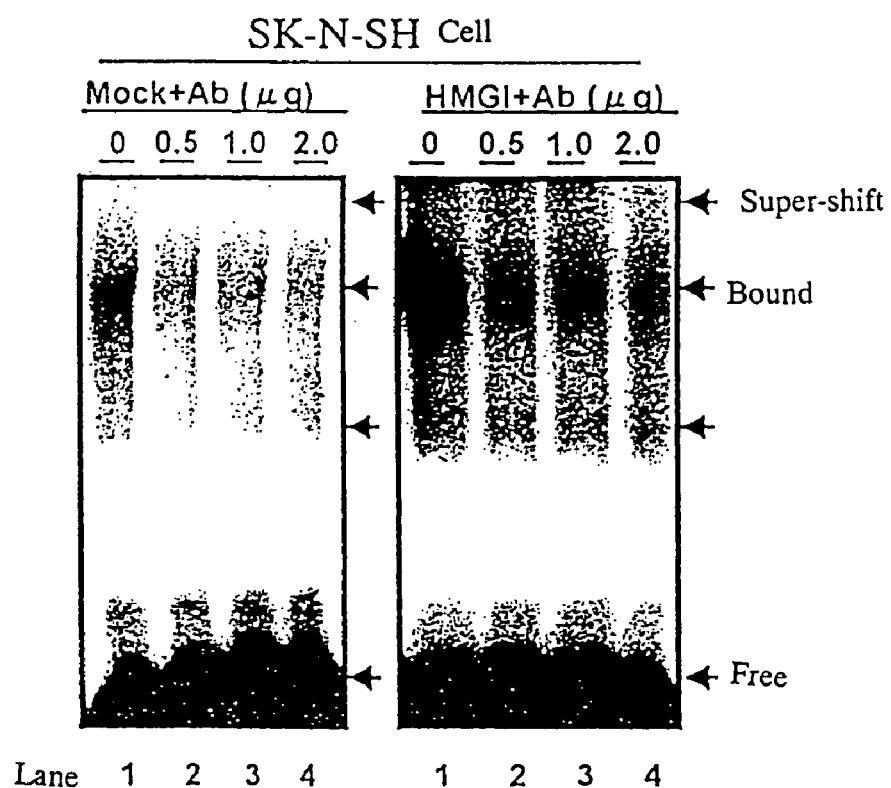

FIG. 18 is a diagram showing the results of examination of the effect of HMG-I ("HMGI" in the figure) on the binding of U1 (70 K) snRNP to PS2 pre-mRNA. Prior to the nuclear extract derived from the collected cells was reacted with ($^{32}$P-labeled) Probe No. 12 (SEQ ID NO: 26) shown in the upper panel, the nuclear extract was incubated in a usual buffer in the presence or absence of an antibody against HMG-I/Y protein. Next, the sample was subjected to gel retardation electrophoresis and autoradiography. In the figure, the solid arrows indicate the free probe, bound probe and super shift probe. Also, in the figure, Ab represents an anti-U1 snRNP antibody. These experiments were repeated at least four times using different cell cultures, and the same results were obtained.

FIG. 19 is a diagram showing an interaction between HMG-I/Y and U1 (70 K) snRNP. The upper panel shows the results of immunoblot assay with an anti-U1 (70 K) snRNP antibody. SK-N-SH cells exposed to normoxia or hypoxia were collected after 24 hours of stimulation to prepare a nuclear extract. The nuclear extract was immunoprecipitated with an anti-HMG-I/Y antibody ("anti-HMGI/Y antibody" in the figure), followed by immunoblot assay with an anti-U1 (70 K) snRNP antibody. The lower panel shows the results of immunoblot assay with an anti-HMG-I/Y antibody. The nuclear extract was immunoprecipitated using an anti-U1 (70 K) snRNP antibody and then subjected to immunoblot assay using an anti-HMG-I/Y antibody. These experiments were repeated at least three times using different cell cultures, and the same results are obtained.

Figure 20:
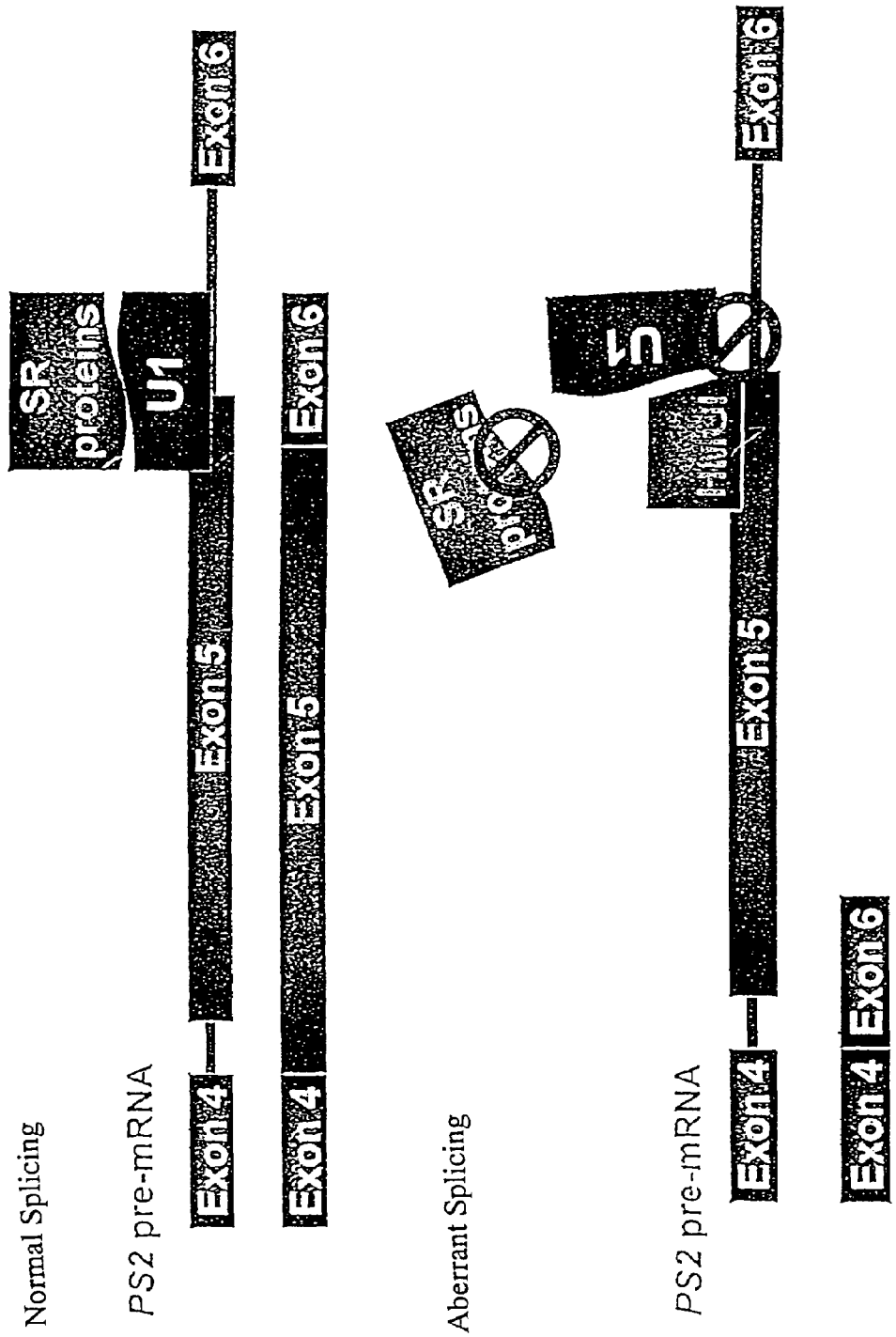

FIG. 20 is a schematic diagram of a hypothesis for a mechanism of aberrant splicing on PS2 pre-mRNA.

Figure 21:
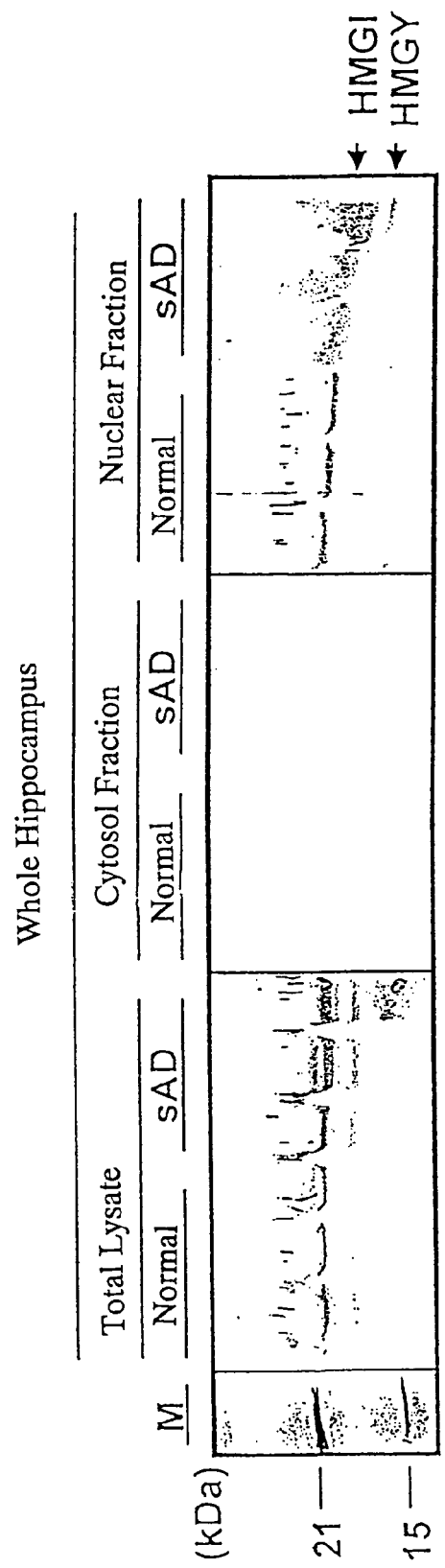

FIG. 21 is a diagram showing the results of examination of expression of HMG-I/Y protein in the sAD brain by Western blot analysis. The total lysate, cytosol fraction and nuclear fraction were prepared from three different sAD brains and age-matching control hippocampuses. These fractions were subjected to SDS-PAGE and to immunoblot assay using an antibody against HMG-I/Y protein. The solid arrows indicate points of the molecular weights corresponding to HMG-I (upper band, "HMGI" in the figure) and HMG-Y (lower part, "HMGY" in the figure) proteins.

FIG. 22 is a diagram showing the results of examination of expression of HMG-I/Y protein in the sAD brain by immunohistochemistry. At least three kinds of different control and AD brains were analyzed, and the same results were always obtained. Brain sections for control and sAD of 10 μm in thickness were prepared, and subjected to an immunohistochemical detection of immunoreactive HMG-I/Y. At least three different kinds of control and AD brains were analyzed, and the same results were always obtained.

FIG. 23 is a diagram showing each synthesized oligonucleotide, which was carried out by a conventional method. Annealing was carried out using two complementary oligonucleotides having bases in length of 24-mer or 60-mer to give each of double-stranded DNA No. 1 to No. 11 (SEQ ID NOS: 13-23 are the 5' to 3' sequences and SEQ ID NOS: 70-80 are the 3' to 5' sequences). In the figure, each fragment of exon 5 of PS2 is underlined and shown in bold letters in each oligonucleotide.

FIG. 24 is a diagram showing a sequence of synthetic DNA for determining a DNA recognition motif of HMG-I (SEQ ID NOS: 28-64). The uppermost row shows a consensus sequence of the HMG-I recognition motif.

FIG. 25 is a diagram showing the results of examination of the action of 2'-O-methyl oligo RNA on the binding of HMG-I to DNA in the nuclear extract derived from SK-N-SH cells. The panel A shows the results of gel shift assay, and the panel B shows data numerically expressing those of the panel A.

BEST MODE FOR CARRYING OUT THE INVENTION

The present invention is based on the surprising findings made by the present inventors that there exists a proteinous factor for inhibiting normal splicing of presenilin-2 gene, the proteinous factor relating to generation of the splicing variant of presenilin-2 in SK-N-SH cell under hypoxic stimulation which is a condition for appearance of a splicing variant of presenilin-2.

The presenilin-2 gene is a gene which is thought to be one of a causative gene in Alzheimer's disease, wherein the gene encodes a membrane protein existing in the endoplasmic reticulum Golgi body, the protein relating to amyloid metabolism or deposition. The above presenilin-2 gene is constituted by 12 exons, out of which 10 exons encode a protein [see, for instance, Levy-Lahad et al., *Genomics*, 34, 198-204 (1996); Levy-Lahad et al., *Science*, 269, 973-977 (1995); Rogaev et al., *Nature*, 376, 775-778 (1995), and the like]. A nucleotide sequence of the presenilin-2 gene and the amino acid sequence thereof are described in, for instance, Accession Nos. XM002127, XM002128, XP002127 or the like in GenBank.

According to the present invention, there are provided the information on the factor relating to the generation of a splice variant that lacks exon 5 of presenilin-2 gene observed in sporadic Alzheimer's disease, and the information on a region in which the factor is associated to bind to the presenilin-2 gene. Accordingly, there is provided a target for treatment and/or prevention of diseases caused by aberrant splicing on the basis of the factor or the inhibitory mechanism for binding.

The "factor relating to generation of a splice variant that lacks exon 5 of presenilin-2 gene" includes, for instance, a factor which is identified as HMG-I by the present inventors, as set forth the Examples given below.

The nucleic acid of the present invention is a nucleic acid consisting of a sequence of a region (referred to as binding region) in which the above "factor relating to generation of a splice variant that lacks exon 5 of presenilin-2 gene" is associated to bind to presenilin-2 mRNA, or a nucleic acid comprising a sequence of the binding region. Concretely, the nucleic acid of the present invention is:

① a nucleic acid capable of binding to HMG-I protein, wherein the nucleic acid causes presenilin-2 gene exon 5-lacked type aberrant splicing by the association with the HMG-I protein, or ② a nucleic acid capable of binding to HMG-I protein, wherein the nucleic acid is a part of a presenilin-2 mRNA precursor.

In the present specification, "a part of a presenilin-2 mRNA precursor" refers to a portion consisting of preferably from 10 to 100 bases in length, more preferably 10 to 50 bases in length and still more preferably 10 to 42 bases in length in the sequence of the presenilin-2 mRNA precursor.

Concretely, one of the significant features of the nucleic acid of the present invention resides in that the nucleic acid binds to the HMG-I protein and comprises (i) the nucleotide sequence shown in SEQ ID NO: 1 and/or (I) the nucleotide sequence shown in SEQ ID NO: 2. Since the nucleic acid of the present invention comprises the nucleotide sequence of the above (i) or (I), the nucleic acid is recognized by and bound to the HMG-I protein.

Since the nucleic acid of the present invention comprises the nucleotide sequence of (i) and/or the nucleotide sequence of (I), the nucleic acid is capable of binding to the "factor relating to generation of a splice variant that lacks exon 5 of presenilin-2 gene." Therefore, there is exhibited an excellent effect that the nucleic acid can be used for screening, for instance, a substance capable of inhibiting the binding between HMG-I and presenilin-2 mRNA by using as an index the presence or absence of binding of the nucleic acid to the above "factor relating to generation of a splice variant that lacks exon 5 of presenilin-2 gene" or the binding strength of the binding (for instance, binding affinity or the like).

The nucleic acid of the present invention may be a mutant of the above "nucleic acid comprising the nucleotide sequence shown in SEQ ID NO: 1 and/or the nucleotide sequence shown in SEQ ID NO: 2" as long as the nucleic acid shows binding affinity of the equivalent level to the binding affinity between HMG-I and the nucleic acid comprising the nucleotide sequence of (i) and/or the nucleotide sequence of (I).

Concretely, the nucleotide sequence corresponding to the above (i) may be, for instance, (ii) a nucleotide sequence having mutation(s) of at least one residue, one or more residues, in the nucleotide sequence shown in SEQ ID NO: 1; (iii) a nucleotide sequence of a nucleic acid capable of hybridizing under stringent conditions to a nucleic acid consisting of the nucleotide sequence shown in SEQ ID NO: 1; or (iv) a nucleotide sequence having at least 90%, preferably 95% or more sequence identity to the nucleotide sequence shown in SEQ ID NO: 1.

Also, the nucleotide sequence corresponding to the above (I) may be, for instance, (II) a nucleotide sequence having mutation(s) of at least one residue, one or more residues, in the nucleotide sequence shown in SEQ ID NO: 2, (III) a nucleotide sequence of a nucleic acid capable of hybridizing under stringent conditions to a nucleic acid consisting of the nucleotide sequence shown in SEQ ID NO: 2, or (IV) a nucleotide sequence having at least 90%, preferably 95% or more sequence identity to the nucleotide sequence shown in SEQ ID NO: 2.

In other words, the nucleic acid of the present invention encompasses a nucleic acid comprising one member selected from the group consisting of the followings 1 and 2:

1. one kind of a nucleotide sequence selected from the group consisting of the above (ii) to (iv), and
2. one kind of a nucleotide sequence selected from the group consisting of the above (II) to (IV), as long as the nucleic acid is a nucleic acid binding to HMG-I protein, wherein the nucleic acid shows a binding affinity of the equivalent level to the binding affinity between HMG-I protein and the nucleic acid comprising one member selected from the group consisting of the nucleotide sequence of (i) and the nucleotide sequence of (I).

The above mutant may be those obtained by introducing mutation at a desired position according to a conventional site-directed mutagenesis, or may be those obtained by synthesizing the desired sequence by a conventional nucleic acid synthesis method. Also, the above mutant includes naturally occurring mutants.

The number of mutations of residues in one member selected from the group consisting of the nucleotide sequence of the above (i) and the nucleotide sequence of the above (I) is appropriately selected within the range in which the nucleic acid having the mutation exhibits a binding affinity of the equivalent level to that of the binding affinity between the HMG-I protein and the nucleic acid comprising one member selected from the group consisting of the nucleotide sequence of (i) and the nucleotide sequence of (I).

The above site-directed mutagenesis includes, for instance, gapped duplex method [see, for instance, *Nucleic Acids Research*, 12, 9441-9456 (1984) or the like], Kunkel method [see, for instance, *Proc. Natl. Acad. Sci. USA*, 82, 488-492 (1985) or the like], a PCR method using primers for mutagenesis, and the like.

The above nucleic acid synthesis method includes, for instance, a triphosphate method, a phosphoramidite method, a H-phosphonate method and the like.

The above "stringent conditions" include, for instance, hybridization conditions described in Sambrook et al., *Molecular Cloning: A Laboratory Manual 2nd Edition* (1989), and the like. Concretely, there are included, for instance, those conditions of carrying out incubation at 60° C. for 12 to 20 hours in a solution containing 6×SSC (1×SSC shows 0.15 M NaCl, 0.015 M sodium citrate, pH 7.0), 0.5% SDS, 5×Denhardt's, and 0.01% denatured salmon sperm nucleic acid.

The above "nucleic acid capable of hybridizing under stringent conditions" can be obtained, for instance, by incubating a nucleic acid to be tested and a nitrocellulose membrane immobilized with either one of a nucleic acid consisting of the nucleotide sequence shown in SEQ ID NO: 1 or a nucleic acid consisting of the nucleotide sequence shown in SEQ ID NO: 2, in a solution containing 6×SSC (1×SSC shows 0.15 M NaCl, 0.015 M sodium citrate, pH 7.0), 0.5% SDS, 5×Denhardt's and 0.01% denatured salmon sperm nucleic acid at 60° C. for 12 to 20 hours, washing the resulting membrane with 2×SSC containing 0.5% SDS at 37° C., and further washing the membrane until a signal ascribed to the immobilized nucleic acid can be distinguished from the background under the conditions in which the SSC concentrations are changed in the range of down to 0.1 times and the temperatures are changed in the range up to 50° C., thereby selecting a nucleic acid showing the signal. By carrying out the hybridization under the stringent conditions, there can be obtained, for instance, a nucleic acid having at least about 90%, preferably 95% or more sequence identity to the nucleotide sequence shown in SEQ ID NO: 1; a nucleic acid having at least about 90%, preferably 95% or more sequence identity to the nucleotide sequence shown in SEQ ID NO: 2; and the like.

The above "sequence identity" refers to identity in residues between either one of nucleic acid molecules of a nucleic acid molecule consisting of the nucleotide sequence shown in SEQ ID NO: 1 or a nucleic acid molecule consisting of the nucleotide sequence shown in SEQ ID NO: 2 and a nucleic molecule to be compared. The above "sequence identity" can be determined by comparing two nucleotide sequences aligned in an optimal state over the region of the nucleotide sequence to be compared. The numerical value (percentage) of sequence identity can be calculated by determining identical bases existing in both the sequences, determining the number of matching sites, dividing the number of matching sites by a total number of bases in the sequence to be compared, and multiplying the obtained numerical value by 100. The algorism for obtaining an optimal alignment and homology includes, for instance, local homology algorism of Smith et al. [*Add. APL. Math.*, 2, 482 (1981)], homology alignment algorism of Needleman et al. [*J. Mol. Biol.*, 48, 443 (1970)], a homology searching method according to Pearson et al. [*Proc. Natl. Acad. Sci. USA*, 85, 2444 (1988)], and the like. More concretely, there are included a dynamic programming method, a gap penalty method, Smith-Waterman algorism, Good-Kanehisa algorism, BLAST algorism, FASTA algorism and the like.

In the present invention, regarding the above mutant, there can be used a nucleic acid which can be confirmed to have a binding ability to HMG-I protein by evaluating the binding between the nucleic acid and HMG-I protein by conventional techniques used in analysis of a protein-nucleic acid interaction, such as gel shift assay, Southwestern analysis, resonance plasmon interaction analysis and the like.

The length of the nucleic acid of the present invention may be a length within a range in which the nucleic acid comprises one member selected from the group consisting of the followings 1. and 2.:

1. one kind of a nucleotide sequence selected from the group consisting of the above (ii) to (iv); and
2. one kind of a nucleotide sequence selected from the group consisting of the above (II) to (IV), wherein the nucleic acid shows a binding ability to HMG-I. It is desired that the length is preferably from 10 to 100 bases in length, more preferably from 10 to 50 bases in length, still more preferably from 10 to 42 bases in length.

More concretely, the nucleic acid of the present invention includes a nucleic acid capable of binding to HMG-I protein, wherein the nucleic acid comprises a sequence of:

(a) one kind of a nucleotide sequence selected from the group consisting of SEQ ID NOs: 3, 4, 5, 6 and 7, or
(b) a nucleotide sequence having one or more substitutions in one kind of a nucleotide sequence selected from the group consisting of SEQ ID NOs: 3, 4, 5, 6 and 7.

The nucleic acid having a sequence of the above (a) includes, for instance, the following nucleic acids:

a nucleic acid capable of binding to HMG-I protein, wherein the nucleic acid comprises the nucleotide sequence shown in SEQ ID NO: 3 and has at least 42 bases in length, concretely preferably from 42 to 100 bases in length, more preferably 42 to 50 bases in length;

a nucleic acid capable of binding to HMG-I protein, wherein the nucleic acid comprises the nucleotide sequence shown in SEQ ID NO: 4 and has at least 21 bases in length, concretely preferably from 21 to 100 bases in length, more preferably from 21 to 50 bases in length;

a nucleic acid capable of binding to HMG-I protein, wherein the nucleic acid comprises the nucleotide sequence shown in SEQ ID NO: 5 and has at least 19 bases in length, concretely preferably from 19 to 100 bases in length, more preferably from 19 to 50 bases in length;

a nucleic acid capable of binding to HMG-I protein, wherein the nucleic acid comprises the nucleotide sequence shown in SEQ ID NO: 6 and has at least 25 bases in length, concretely preferably from 25 to 100 bases in length, more preferably from 25 to 50 bases in length;

a nucleic acid capable of binding to HMG-I protein, wherein the nucleic acid comprises the nucleotide sequence shown in SEQ ID NO: 7 and has at least 23 bases in length, concretely preferably from 23 to 100 bases in length, more preferably from 23 to 50 bases in length; and the like.

The nucleic acid having the nucleotide of the above (b) includes, for instance, the following nucleic acids:

a nucleic acid capable of binding to HMG-I protein, wherein the nucleic acid comprises the nucleotide sequence having one or more substitutions in the nucleotide sequence shown in SEQ ID NO: 3 and has at least 42 bases in length, concretely preferably from 42 to 100 bases in length, more preferably from 42 to 50 bases in length;

a nucleic acid capable of binding to HMG-I protein, wherein the nucleic acid comprises the nucleotide sequence having one or more substitutions in the nucleotide sequence shown in SEQ ID NO: 4 and has at least 21 bases in length, concretely preferably of from 21 to 100 bases in length, more preferably 21 to 50 bases in length;

a nucleic acid capable of binding to HMG-I protein, wherein the nucleic acid comprises the nucleotide sequence having one or more substitutions in the nucleotide sequence shown in SEQ ID NO: 5 and has at least 19 bases in length, concretely preferably from 19 to 100 bases in length, more preferably from 19 to 50 bases in length;

a nucleic acid capable of binding to HMG-I protein, wherein the nucleic acid comprises the nucleotide sequence having one or more substitutions in the nucleotide sequence shown in SEQ ID NO: 6 and has at least 25 bases in length, concretely preferably from 25 to 100 bases in length, more preferably from 25 to 50 bases in length;

a nucleic acid capable of binding to HMG-I protein, wherein the nucleic acid comprises the nucleotide sequence having one or more substitutions in the nucleotide sequence shown in SEQ ID NO: 7 and has at least 23 bases in length, concretely preferably 23 to 100 bases in length, more preferably 23 to 50 bases in length;

and the like.

Also, an antisense molecule of a nucleic acid having a nucleotide sequence such as the above (i) to (iv), (I) to (IV), (a), (b) or the like (hereinafter also referred to as sense nucleic acid) has a possibility of inhibiting the binding between the sense nucleic acid and the HMG-I protein. The antisense molecule is also encompassed within the scope of the present invention.

According to the antisense molecule of the present invention, since there is a possibility of inhibiting the binding between the sense nucleic acid and the HMG-I protein, for instance, there can be expected to prevent the generation of aberrant splicing caused by binding of the protein to the sense nucleic acid. Therefore, according to the antisense molecule, there is expected treatment and/or prevention of a disease caused by aberrant splicing.

The antisense molecule can be prepared by chemical synthesis or the like.

The above "disease caused by aberrant splicing" includes ALS, FTDP, FAD and the like.

According to the nucleic acid (sense nucleic acid) of the present invention, the inhibitory ability or suppressive ability of the substance to be tested for the above binding can be evaluated by detecting the binding between the nucleic acid and HMG-I protein in the presence of a substance to be tested or determining the binding strength of the binding (for instance, binding affinity or the like).

Therefore, according to the present invention, there is provided a method for screening an inhibitor for the binding between exon 5 of presenilin-2 gene and the HMG-I protein. The method for screening an inhibitor is also encompassed within the scope of the present invention.

In the present specification, the "inhibitor" is intended to encompass both a substance completely inhibiting the binding and a substance reducing a binding strength of the binding (for instance, binding affinity or the like).

One of the significant features of the method screening for an inhibitor of the present invention resides that the method comprises detecting in the presence and absence of a substance to be tested, the binding between the nucleic acid of the present invention (the nucleic acid of the above ① or ②) and HMG-I protein, or determining the binding strength of the binding (for instance, binding affinity or the like), wherein either one of the following I) or II):

I) a case where the binding between the nucleic acid and the HMG-I protein is not detected in the presence of the substance to be tested, or II) a case where the binding strength a of the binding between the nucleic acid and the HMG-I protein in the presence of the substance to be tested is smaller than the binding strength b of the binding between the nucleic acid and the HMG-I protein in the absence of the substance to be tested is used as an index showing that the substance to be tested is an inhibitor of the binding between exon 5 of the presenilin-2 gene and the HMG-I protein.

Concretely, in the method screening for an inhibitor of the present invention, in the case where the above I) is used as an index, there may be carried out a process (referred to as Process 1), comprising the steps of (A) contacting the nucleic acid (sense nucleic acid) of the present invention with HMG-I protein in the presence of a substance to be tested and (B) detecting the binding between the nucleic acid and the HMG-I protein. Alternatively, in the case where the above II) is used as an index, there can be carried out a process (referred to as Process 2) comprising the steps of (a) contacting the nucleic acid (sense nucleic acid) of the present invention with HMG-I protein in the presence and absence of a substance to be tested, and (B) determining a binding strength a between the nucleic acid and the HMG-I protein in the presence of the substance to be tested and a binding strength b between the nucleic acid and the HMG-I protein in the absence of the substance to be tested.

The above substance to be tested may be any one of polypeptides, nucleic acids and other compounds. The above substance to be tested can be subjected to the screening method of the present invention at an appropriate series of dilution.

In the screening method of the present invention, the nucleic acid (sense nucleic acid) of the present invention or the HMG-I protein may be labeled with a detectable labeling substance. The above labeling substance includes conventionally used fluorescent substances, radioactive substances and the like. The labeling of the nucleic acid or the protein can be carried out by conventional techniques. For instance, when the nucleic acid is labeled with the above labeling substance, the nucleic acid can be labeled by, for instance, a method described in Sambrook et al., *Molecular Cloning, A LABORATORY MANUAL/SECOND EDITION*, Cold Spring Harbor Laboratory Press (1989), and the like.

In the step (A) in the above Process 1, the contacting of the nucleic acid (sense nucleic acid) of the present invention with the HMG-I protein in the presence of a substance to be tested can be carried out under the same conditions as those of the binding of the nucleic acid (sense nucleic acid) to the HMG-I protein in the absence of a substance to be tested. Further, the above step (A) may be carried out with suitable modification of the conditions of temperature, buffer and the like within the range in which the binding between the nucleic acid (sense nucleic acid) and the HMG-I protein can be maintained in the absence of the substance to be tested.

In the present specification, the conditions by which the nucleic acid (sense nucleic acid) of the present invention binds to the HMG-I protein in the absence of a substance to be tested are also referred to as "binding conditions".

The above HMG-I protein can be intracellularly expressed, for instance, by culturing an appropriate cell under normoxia conditions and then culturing the cell under hypoxia conditions, to subject them to hypoxic exposure. The above cell includes, for instance, cells in the central nervous system such as nerve cells, glia cells and astral cells; fibroblasts and the like. More concretely, the cell includes, for instance, SK-N-SH cells (ATCC HTB-11) and the like. The normoxia conditions can be appropriately set depending on the cells used, including, for instance, in the case of SK-N-SH cells, the conditions of culturing the cells in 5% $CO_2$ at 37° C. and the like. The hypoxia conditions include, for instance, those of hypoxic pressure (8 torr). Concretely, the cells can be subjected to hypoxic stimulation by exposing the culture to low oxygen at 37° C. for 21 hours in an incubator equipped with a hypoxic chamber maintained in a humidity atmosphere at a hypoxic pressure (8 torr).

In the step (B) in Process 1, the detection of the binding between the nucleic acid (sense nucleic acid) of the present invention and HMG-I protein can be carried out by conventional techniques used in analysis of a protein-nucleic acid interaction, such as the above resonance plasmon interaction analysis and gel shift assay.

For instance, when the detection of the binding between the nucleic acid (sense nucleic acid) of the present invention and HMG-I protein is carried out by the above resonance plasmon interaction analysis, first, a matrix in which the nucleic acid (sense nucleic acid) of the present invention is immobilized on an appropriate support is contacted with HMG-I protein, or a matrix in which HMG-I protein is immobilized on an appropriate support is contacted with a nucleic acid (sense nucleic acid) of the present invention, in the presence of a substance to be tested. Next, a change in mass or a change in fluorescence intensity in the presence of the substance to be tested is determined. Here, if there is no change in mass or in fluorescence intensity, the above binding is not formed, and also that the substance to be tested is an inhibitor of the binding between exon 5 of the presenilin-2 gene and the HMG-I protein.

For instance, when the detection of the binding between the nucleic acid (sense nucleic acid) of the present invention and HMG-I protein is carried out by gel shift assay, a sample suitable for gel shift assay is prepared from the mixture obtained by mixing a substance to be tested, a nucleic acid (sense nucleic acid) of the present invention and HMG-I protein under the above binding conditions, and subjected to gel shift assay. As the control, a binding product obtained by maintaining the nucleic acid (sense nucleic acid) of the present invention and the HMG-I protein under the above binding conditions is used. Either one of the nucleic acid (sense nucleic acid) of the present invention or the HMG-I protein is labeled with the above labeling substance. In addition, when a substance which can prevent the gel shift assay is contained in the above sample, the procedures for removing the substance may be carried out. The above procedures for gel shift assay can be carried out in reference to "*Molecular Biology Protocol,*" Revised 2nd Edition (1999) published by Nankodo or the like with appropriate modifications thereto. Regarding the above sample, when a signal ascribed to the labeling substance is not detected at a position of the same mobility as that of the binding product, it is used as an index that the above binding is not formed, in which it is shown that the substance to be tested is an inhibitor for the binding between exon 5 of presenilin-2 gene and HMG-I protein.

On the other hand, in the step (a) in Process 2, the contacting of the nucleic acid (sense nucleic acid) of the present invention with the HMG-I protein under each of the conditions of the presence and absence of a substance to be tested can be carried out under the same conditions as the binding conditions in the above method screening for an inhibitor.

In the step (b), the determinations of the binding strength a and the binding strength b can be carried out by determining the mass, fluorescence intensity, radioactivity or the like by a conventional technique used in the analysis of a protein-nucleic acid interaction, such as the resonance plasmon interaction analysis or the gel shift assay.

For instance, when the above binding strength a and binding strength b are determined by the above resonance plasmon interaction analysis, first, a matrix in which the nucleic acid (sense nucleic acid) of the present invention is immobilized on an appropriate support is contacted with the HMG-I protein, or a matrix in which the HMG-I protein is immobilized on an appropriate support is contacted with the nucleic acid (sense nucleic acid) of the present invention, in the presence and absence of a substance to be tested. Next, the mass or fluorescence intensity in the presence of the substance to be tested and the mass or fluorescence intensity in the absence of the substance to be tested are determined. Here, when the mass or fluorescence intensity in the presence of the substance to be tested (binding strength a) is lower than the mass or fluorescence intensity in the absence of the substance to be tested (binding strength b), it is shown that the substance to be tested is an inhibitor for the binding between exon 5 of the presenilin-2 gene and the HMG-I protein.

For instance, when the above binding strength a and binding strength b are determined by gel shift assay, a sample suitable for gel shift assay is prepared from the mixture obtained by mixing a substance to be tested, the nucleic acid (sense nucleic acid) of the present invention and HMG-I protein under the binding conditions described above, and subjected to gel shift assay. Either one of the nucleic acid (sense nucleic acid) of the present invention or HMG-I protein is labeled with the labeling substance. Next, the intensity of a signal ascribed to the above labeling substance at the position of the binding product is determined in the presence and absence of the substance to be tested. The intensity of the signal can be determined by a commonly used densitometer or the like. Here, when the mass or fluorescence intensity in the presence of the substance to be tested (binding strength a) is smaller than the mass or fluorescence intensity in the absence of the substance to be tested (binding strength b), it is shown that the substance to be tested is an inhibitor for the binding between exon 5 of the presenilin-2 gene and the HMG-I protein.

In the method for screening an inhibitor of the present invention, there may be further carried out the steps of determining the binding between HMG-I protein and a DNA having the nucleotide sequence shown in SEQ ID NO: 66 in the presence of a substance to be tested, and selecting a compound not inhibiting the binding. By carrying out the above steps, there are exhibited excellent effects that an inhibitor not being affected by a loss in the inherent function can be selected based on the binding between HMG-I and DNA.

According to the method for screening an inhibitor of the present invention, there can also be carried out pharmacological evaluation on the inhibitor of the binding between the nucleic acid (sense nucleic acid) of the present invention and the HMG-I protein. Especially, according to the above Process 2, a suppressive ability for the binding by the inhibitor can also be evaluated.

The inhibitor obtained according to the method for screening an inhibitor of the present invention is also encompassed within the scope of the invention.

The inhibitory ability or suppressive ability for the binding regarding the inhibitor can be evaluated by examining, for instance, the index of the above I) or II) in the presence of the inhibitor in the same manner as in the above method for screening the inhibitor.

EXPERIMENTAL EXAMPLE 1

Cell Culture, Hypoxic Stimulation and Transient Transfection

According to a literature by Sato et al. [Sato N. et al., *J. Biol. Chem.*, 276, 2108-2114 (2001)], cell culture and hypoxic stimulation were carried out in the following manner.

Human neuroblastoma SK-N-SH cells were cultured in 5% $CO_2$ at 37° C. in αMEM (manufactured by GIBCO BRL) containing 10% fetal bovine serum. When the above cells achieved confluence in a 176.6 $cm^2$ culture plate, the serum-containing α-MEM in the culture was exchanged with serum-free αMEM. The culture obtained after medium exchange was further cultured for 4 hours.

HEK-293T Cells and HeLa cells were cultured respectively in 5% $CO_2$ at 37° C. in a Dulbecco's minimum essential medium (manufactured by GIBCO BRL) containing 10% fetal bovine serum. When each of the above cells achieved confluence in a 176.6 $cm^2$ culture plate, the serum-containing Dulbecco's minimum essential medium in the culture was exchanged with a serum-free Dulbecco's minimum essential medium. The culture obtained after medium exchange was further cultured for 4 hours.

In the case of hypoxic stimulation, the resulting culture was exposed to hypoxia at 37° C. for 21 hours in an incubator equipped with a hypoxic chamber maintained in a humidified atmosphere with a low oxygen pressure (8 torr).

Transient transfection of various constructs was carried out by using LepofectAMINE™ 2000 (manufactured by GIBCO BRL).

EXPERIMENTAL EXAMPLE 2

Preparation of Total RNA and RT-PCR

According to literature by Sato et al. [Sato N. et al., *J. Neurochem.*, 72, 2498-2505 (1999)], preparations of total RNAs from neuroblastoma SK-N-SH cells, HEK-293T cells and HeLa cells under various stresses, and RT-PCR were carried out in the following manner.

Total RNAs were extracted and purified from SK-N-SH cells and HEK-293T cells under normoxia conditions, upon exposure to hypoxia, or at the time of overexpression of HMG-I, by using an RNeasy total RNA kit (manufactured by Qiagen) according to manufacture's instructions.

Then, the resulting total RNA and a mouse molony leukemia virus reverse transcriptase (manufactured by Promega) were used, to perform reverse transcription at 42° C. for 1 hour. Subsequently, using the resulting reaction product as a template, nested PCR was carried out. A thermal profile of PCR is 30 cycles, wherein one cycle consists of reactions at 95° C. for 30 seconds, 60° C. for 30 seconds and 72° C. for 1 minute (2 minutes in the final cycle). In the 1st PCR, primer ps251 (5'-attcagacctctctgcggcc-3' [SEQ ID NO: 9]) and primer ps231 (5'-aagcgggagccaaagtctgg-3' [SEQ ID NO: 10]). In the 2nd PCR, primer ps252 (5'-gttcgtggtgcttccagagg-3' [SEQ ID NO: 11]) and primer ps233 (5'-ggaccactctgggaggtaca-3' [SEQ ID NO: 12]) were used.

The resulting product was electrophoresed on 5% polyacrylamide gel and visualized by staining with ethidium bromide.

EXPERIMENTAL EXAMPLE 3

Preparation of Nuclear Extract

According to a modified method of a method by Shreiber et al. [Yoneda, Y. et al., *Neuroscience*, 90, 519-533 (1999)], a nuclear extract was prepared in the following manner.

All of the buffer and other solutions used were sterilized each time prior to use by filtration with Steritop (manufactured by Millipore) having a pore size of 220 nm.

Unless otherwise specified, each cell construct was homogenized at 2° C. in 50 volumes [315 μl/plate] of 10 mM HEPES-NaOH buffer (pH 7.9) containing 10 mM KCl, 1 mM EDTA, 1 mM EGTA, 5 mM dithiothreitol (DTT) and 1 mM (p-amidinophenyl)methanesulfonyl fluoride (PMSF).

Then, 10% Nonidet P-40 was added at a final concentration of 0.6% to the resulting homogenate. The resulting mixture was centrifuged at 15000 rpm for 5 minutes. Then, the resulting pellet was suspended in 10 volumes [0.1 ml] of 20 mM Tris-HCl (pH 7.5) containing 400 mM KCl, 1 mM EDTA, 1 mM EGTA, 1 mM DTT and 1 mM PMSF, and then cooled on ice for 30 minutes. The suspension obtained after cooling on ice was centrifuged at 15000 rpm for 5 minutes. The resulting supernatant was used as a nuclear extract for pre-mRNA binding assay, gel shift assay and supershift assay. The above nuclear extract was stored at −80° C. before use.

EXPERIMENTAL EXAMPLE 4

Preparation of Cytosol Fraction and Nuclear Fraction

According to a literature by Manabe et al. [Manabe et al., *Neuroscience*, 100, 453-463 (2000)], a nuclear fraction was prepared in the following manner.

A brain structure was homogenized at 2° C. in 10 mM HEPES-NaOH buffer (pH 7.9) [315 µl/plate] containing 10 mM KCl, 1 mM EDTA, 1 mM EGTA, 5 mM DTT and 1 mM PMSF. 10% Nonidet P-40 was added at a final concentration of 0.6% to the resulting homogenate. The resulting mixture was centrifuged at 15000 rpm for 5 minutes, to give a pellet [nuclear fraction (insoluble in NP-40)] and a supernatant [cytosol fraction (soluble in NP-40)]. The above pellet was suspended in 50 mM Tris-HCl (pH 7.5) [50 µl] containing 1 mM EDTA, 1 mM EGTA and PMSF, to give a nuclear fraction (insoluble in NP-40).

EXPERIMENTAL EXAMPLE 5

Preparation of DNA Constructs

The respective oligonucleotides shown in FIG. 23 were synthesized according to a conventional method. Two complementary oligonucleotides each having a nucleotide length of a 24-mer or 60-mer were used in annealing, to give double-stranded DNA fragments of Nos. 1 to 11 (SEQ ID NOs: 13 to 23). In the Figure, each fragment of PS2 exon 5 is underlined and shown in bold letters in each oligonucleotide.

Each of the resulting double-stranded DNA fragments was incorporated into pcDNA vector, to give DNA constructs. Each of the above double-stranded DNA fragments was sequenced by using a DNA sequencer type 373A (manufactured by Applied Biosystem).

EXPERIMENTAL EXAMPLE 6

Preparation of Pre-mRNA Probes

The DNA constructs obtained in Experimental Example 5 were linearized with EcoRI, to give template DNAs. The above template DNAs were then subjected to in vitro transcription by incubation at 37° C. for 1 hour in a transcription buffer containing [$\alpha$-$^{35}$S]-labeled UTP (62.5 µCi) or [$\alpha$-$^{32}$P]-labeled UTP (50 µCi), 0.25 mM UTP, 0.5 mM ATP, 0.5 mM CTP, 0.5 mM GTP, a T7 RNA polymerase buffer, 20 U of T7 RNA polymerase (manufactured by Promega) and 40 U of RNase inhibitor (manufactured by Toyobo), to give pre-mRNA probes (RNA probes of Nos. 1 to 11).

EXPERIMENTAL EXAMPLE 7

Pre-mRNA Binding Assays

The nuclear extract of an amount equivalent to 5 µg of protein was incubated with 10 µg tRNA and each of $^{35}$S-labeled RNA probes (1 µg) at 25° C. for 30 minutes in an incubation buffer (12 mM HEPES-NaOH buffer [pH 7.9] containing 60 mM KCl, 4 mM MgCl$_2$, 1 mM EDTA, 1 mM EGTA, 1 mM DTT, 10% glycerol and 1 mM PMSF) (total volume 25 µl).

Then, the resulting reaction product was irradiated with ultraviolet (UV) rays for 15 minutes at room temperature under an UV irradiation equipment (254 nm, 60 W). Thereafter, 10 µg RNase A was added to the reaction product after irradiation with UV rays, and then incubated at 25° C. for 30 minutes, to digest the probe in the above reaction product.

The resulting product was treated with sodium dodecyl sulfate (SDS) by mixing it in a volume ratio of 1:4 with 10 mM Tris-HCl buffer (pH 6.8) containing 10% glycerol, 2% SDS, 0.01% Bromophenol Blue and 5% 2-mercaptoethanol.

The solution treated with SDS was subjected to electrophoresis on 10 to 20% gradient polyacrylamide gel and 15% polyacrylamide gel each containing 0.1% SDS at a constant current of 15 mA/plate for 2 hours at room temperature. The gel obtained after the electrophoresis was fixed, dried and exposed to an imaging plate.

EXPERIMENTAL EXAMPLE 8

Northern Blot Assays

According to a method described in the above literature by Sato et al. [Sato N. et al., *J. Biol. Chem.*, 276, 2108-2114 (2001)], Northern blot assays were carried out in the following manner. Specifically, an amount equivalent to 20 µg of total RNA was electrophoresed on formaldehyde-formamide gel, and the resulting gel was blotted onto a nylon filter. Then, the RNA transferred onto the above nylon filter was hybridized with labeled human HMG-I cDNA. The above labeled human HMG-I cDNA was prepared by labeling with Random-Labeling kit (manufactured by Takara Shuzo).

EXPERIMENTAL EXAMPLE 9

Immunoblot Assays

According to the above literature by Manabe et al. [Manabe et al., *Neuroscience*, 100, 453-463 (2000)], immunoblot assays were carried out in the following manner. Specifically, the amount of proteins in each of the nuclear extract, the whole lysate, the cytosol fraction and the nuclear fraction was measured. Then, an aliquot of each of the nuclear extract, the whole lysate, the cytosol fraction and the nuclear fraction was mixed in a volume ratio of 1:4 with a buffer [10 mM Tris-HCl, 10% glycerol, 2% sodium dodecyl sulfate (SDS), 0.01% Bromophenol Blue, 5% mercaptoethanol, (pH 6.8)]. The resulting mixture was boiled at 100° C. for 10 minutes. A given amount of each aliquot (an amount equivalent to 25 µg of protein for the nuclear extract or 50 µg of protein for the whole lysate, cytosol fraction or nuclear fraction) was electrophoresed on 15% polyacrylamide gel containing 0.1% SDS at a constant current of 15 mA/plate for 2 hours at room temperature. Each gel after electrophoresis was blotted onto a polyvinylidene difluoride (PVDF) membrane activated with 100% methanol. The PVDF membrane obtained after blotting was blocked with PBS containing 0.05% Tween-20 and 5% skim milk. Then, the PVDF membrane was reacted with an anti-HMG-I/Y antibody diluted with PBS containing 0.05% Tween-20 in which 1% skim milk was contained. The PVDF membrane was then reacted with an alkaline phosphatase-conjugated anti-goat immunoglobulin G (IgG) antibody. The immunoreactivity was visualized in 100 mM Tris-HCl buffer (pH 9.5) containing 100 mM NaCl, 5 mM MgCl$_2$, 66.7% 4-nitro blue tetrazolium chloride (NTB) and 33.3% X-phosphate/5-bromo-4-chloro-3-indolyl phosphate (BCIP).

EXPERIMENTAL EXAMPLE 10

Immunoprecipitation

According to a method described in the above literature by Sato et al. [Sato N. et al., *J. Biol. Chem.*, 276, 2108-2114 (2001)], immunoprecipitation was carried out in the following manner.

The nuclear extract derived from SK-N-SH cells under normoxia or the nuclear extract derived from SK-N-SH cells exposed to hypoxia was incubated at 4° C. for 8 hours with an anti-HMG-I antibody (manufactured by Santa Cruz Biotechnology). The resulting product was mixed with protein-G agarose (manufactured by Pharmacia Biotech) and kept at 4° C. for 1 hour. The resulting mixture was centrifuged at 3000 rpm for 5 minutes, and the resulting precipitates were suspended in PBS. Further, the resulting suspension was centrifuged at 3000 rpm for 5 minutes. The resulting precipitates were suspended in Mili-Q water. This suspension was treated with SDS, and the resulting solution was subjected to SDS-PAGE. The resulting gel was subjected to immunoblot assay using an antibody against U1 (70 K) snRNP.

Also, the nuclear extracts were subjected to immunoprecipitation using an anti-U1 (70 K) snRNP antibody (manufactured by Santa Cruz Biotechnology) in place of the above anti-HMG-I antibody, and then subjected to immunoblot assay using an antibody against HMG-I/Y (anti-HMG-I/Y antibody, manufactured by Santa Cruz Biotechnology) in place of the above antibody against U1 (70 K) snRNP.

EXPERIMENTAL EXAMPLE 11

Immunocytochemistry

The immunocytochemistry of SK-N-SH cells was carried out. Specifically, SK-N-SH cells were maintained under normoxia conditions, or the cells were exposed to hypoxic conditions for 21 hours. Then, the resulting cells were fixed in 4% paraformaldehyde at room temperature for 2 hours and permeated in 0.3% Triton-X100 for at least 5 minutes. The fixed and permeated cells were washed 3 times with PBS. The washed cells were subjected to immunoreaction using an anti-HMG-I/Y antibody and anti-SC35 antibody (manufactured by Sigma) at 4° C. for 12 hours. The cells were washed 3 times with PBS and incubated with FITC-conjugated anti-goat IgG antibody and Cy3-conjugated anti-mouse IgG antibody at room temperature for 2 hours. The immunoreactive protein was observed with a 488 nm excitation filter under a microscope equipped with a computer.

EXPERIMENTAL EXAMPLE 12

Immunohistochemistry

An immunohistochemical method was carried out by using a modified immunoperoxidase method described in the above literature by Sato et al. [Sato N. et al., *J. Biol. Chem.*, 276, 2108-2114 (2001)]. Specifically, a control or an sAD brain section was fixed at room temperature for 2 hours, and then treated for HMG-I/Y immunohistochemistry. The anti-HMG-I/Y antibody or anti-SS MAG antibody was used at a dilution of 1:1000. A biotinylated anti-goat antibody or biotinylated anti-rabbit IgG (manufactured by Vectastain Elite) was used as a secondary antibody. Immunoreactivity was visualized with 0.05% DAB and 0.01% hydrogen peroxide in 50 mM Tris (pH 7.6).

EXPERIMENTAL EXAMPLE 13

Super Shift Assay

A nuclear extract of an amount equivalent to 5 μg of protein was pretreated by incubation at 4° C. for 8 hours with 1 μg anti-HMG-I/Y antibody (manufactured by Santa Cruz Biotechnology) or 0.5 to 2.0 μg anti-U1 (70 K) snRNP antibody (manufactured by Santa Cruz Biotechnology). The resulting pretreated product was incubated with 2 μg or 10 μg tRNA in an incubation buffer [composition: 12 mM HEPES-NaOH buffer (pH 7.9) containing 60 mM KCl, 4 mM $MgCl_2$, 1 mM EDTA, 1 mM EGTA, 1 mM DTT, 10% glycerol and 1 mM PMSF]. Then, $^{32}$P-labeled RNA probe [1 μg, the probe of No. 5 shown in FIG. 4] was added thereto and incubated at 25° C. for 30 minutes (total volume 50 μl).

The resulting reaction product was electrophoresed at a constant voltage of 11 V/cm for 1.5 hours at 4° C. on 4% polyacrylamide gel in a buffer (pH 8.5) containing 50 mM Tris, 0.38 M glycine and 2 mM EDTA, whereby the bound probe was separated from the free probe. After electrophoresis, the gel was fixed, dried and then exposed to an X-ray film.

EXAMPLE 1

Expression of PS2V in Brain of Patient with Sporadic Alzheimer's Disease and in Cultured Cells (1) Expression of PS2V in Brain of a Patient Brain with Sporadic Alzheimer's Disease The total RNA derived from the brain of a patient with sporadic Alzheimer's disease (sAD) or the total RNA derived from a control brain of an age-matched patient was assayed by RT-PCR.

According to a method described by Anwar R. et al. (Anwar R. et al., *J. Neurochem.*, 66, 1774-1777 (1996)), mRNA was isolated from the sAD brain and the control brain.

Then, the resulting mRNA and a mouse molony leukemia virus reverse transcriptase (manufactured by Promega) were used, to perform reverse transcription reaction. The thermal profile of PCR is 30 cycles, wherein one cycle consists of denaturation: 95° C., 2 minutes/95° C., 30 seconds, annealing: 60° C., 30 seconds and extension: 72° C., 1 minute. In addition, as the 1st primers, the above primers ps251 and ps231 were used, and as the 2nd primers, the primers ps252 and ps233 were used.

The resulting reaction product was electrophoresed on 5% polyacrylamide gel. The amplified product was visualized by staining with ethidium bromide. The results are shown in FIG. 1.

Figure 1:
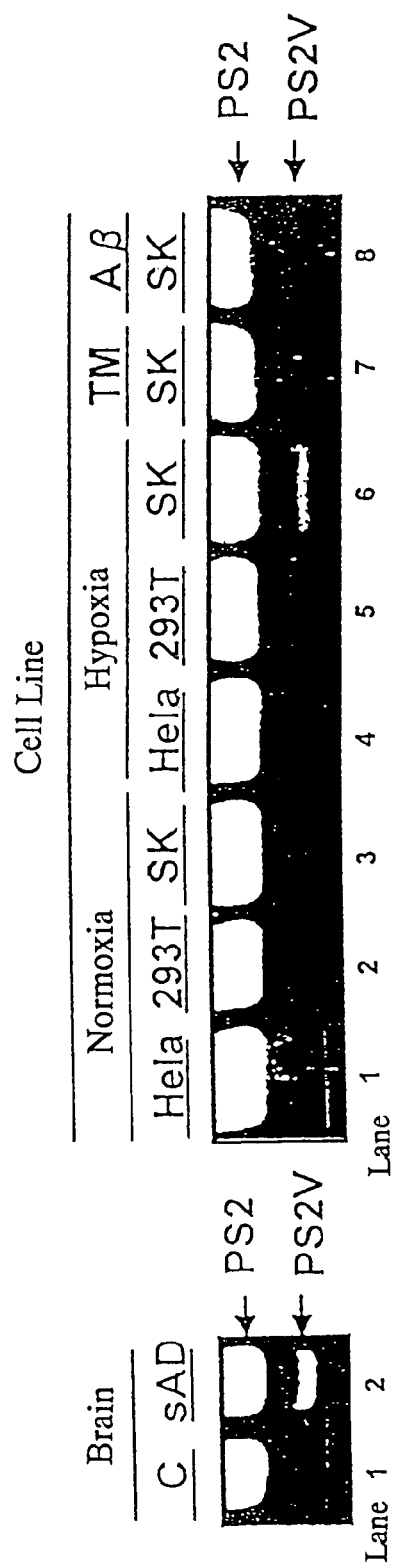
FIG. 1 is a diagram showing expression of PS2V in a sAD brain and cultured cell lines. The left panel is the results of separating an amplified product from a representative sAD brain or from an age-matching control brain on a polyacrylamide gel and visualizing by staining with ethidium bromide. The right panel is the results of subjecting total RNAs to RT-PCR, wherein the total RNAs derived from various cells under normoxia or various stresses such as hypoxic exposure, tunicamycin (TM) and β-amyloid, separating the resulting PCR product on a polyacrylamide gel, and visualizing by staining with ethidium bromide. In the figure, the solid arrows indicate points of the molecular weights corresponding to PS2 (upper part) and PS2V (lower part), respectively. These experiments are repeated at least four times using different cell cultures, and the same results are obtained.

As shown in lane 1 in the left panel in FIG. 1 and in the literature by Sato et al. [Sato et al., *J. Neurochem.*, 72, 2498-2505 (1999)], the full-length PS2 can be detected as the major RT-PCR product in the control brain. On the other hand, as shown in lane 2 in the left panel in FIG. 1, a shorter chain product, in addition to the full-length PS2, can be detected in the sAD brain. As a result of direct sequencing, it is revealed that the above shorter chain product is a variant that lacks exon 5 of PS2 gene (hereinafter, referred to as PS2V).

(2) Expression of PS2V in Cultured Cells

For efficiently reproducing the production of PS2V in cultured cells as in the sAD model, total RNAs derived from various cell lines under various stresses were determined for expression of PS2V in the same experiment as mentioned above. The results are shown in the right panel in FIG. 1.

As shown in lanes 1 to 3 in the right panel in FIG. 1, only the full-length PS2 is detected in various cell lines, namely, HeLa cells, HEK-293T cells and SK-N-SH cells which are exposed to normoxia conditions, respectively. Also, as shown in lanes 4 and 5 in the right panel in FIG. 1, the same results are shown in HeLa cells and HEK-293T cells exposed to hypoxic conditions.

However, it is found that PS2, and a short chain product confirmed to be PS2V by direct sequencing, are detected in SK-N-SH cells exposed to hypoxic conditions [lane 6 in the right panel in FIG. 1; Sato et al., *J. Neurochem.*, 72, 2498-2505 (1999)] and in the sAD brain.

On the other hand, detectable PS2V was not observed under other stresses, namely, tunicamycin (lane 7 in the right panel in FIG. 1), β-amyloid (lane 8 in the right panel in FIG. 1) and hydrogen peroxide [Sato et al., *J. Neurochem.*, 72, 2498-2505 (1999)].

Then, the localization of PS2V was examined by immunohistochemical staining using an antibody against PS2V protein (anti-SSMAG antibody). The results are shown in FIG. 2.

As shown in FIG. 2 and in the literature by Sato et al. [Sato N. et al., *J. Biol. Chem.*, 276, 2108-2114 (2001)], the immunoreactivity to PS2V is observed in a pyramidal cell layer in a hippocampus CA1 region and a pyramidal cell layer in a temporal cortex in sAD brain tissues. Accordingly, it is found that PS2V is localized in a pyramidal cell layer in a hippocampus CA1 region and a pyramidal cell layer in a temporal cortex in sAD brain tissues.

EXAMPLE 2

Detection of PS2 Pre-mRNA-binding Factor in Hypoxia-exposed Cells

Figure 3:
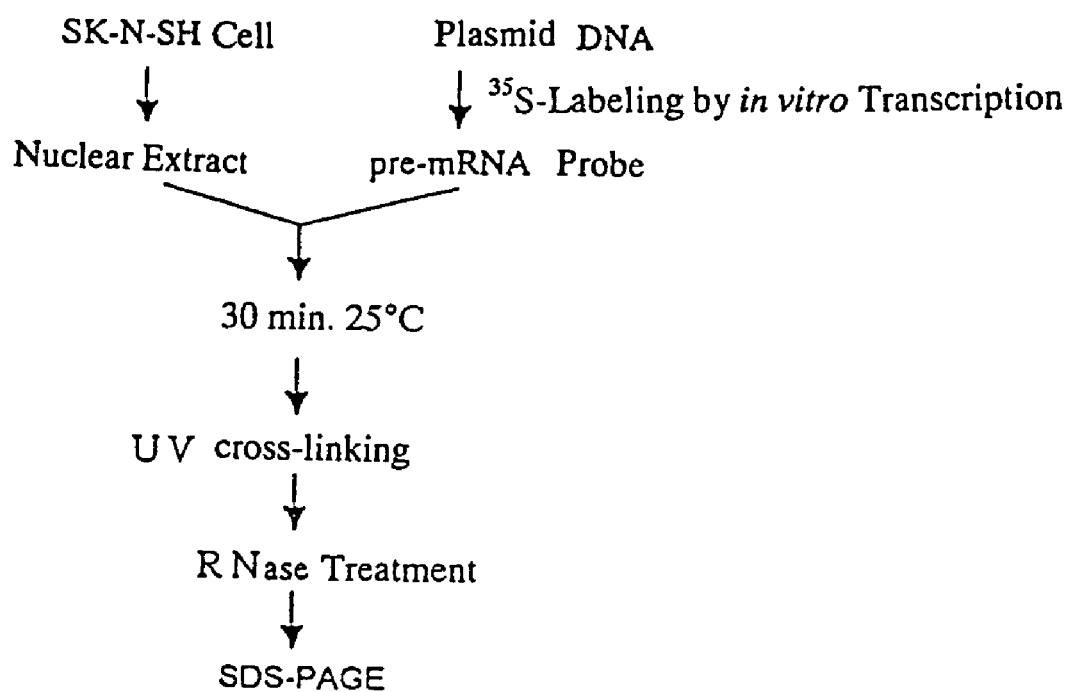
FIG. 3 is a diagram showing a scheme of pre-mRNA binding assay. SK-N-SH cells are collected 21 hours after normoxia or hypoxic stimulation, followed by a preparation of a nuclear extract, and subsequent binding reaction with each probe of PS2 pre-mRNA fragments. The reaction solution is irradiated with ultraviolet (UV) rays. Thereafter, the probe is digested with RNase A, and the digest is subjected to SDS treatment. The SDS-treated sample is separated by SDS-PAGE assay, and thereafter a binding-positive band is detected by using a Bas imaging plate.
Figure 4:
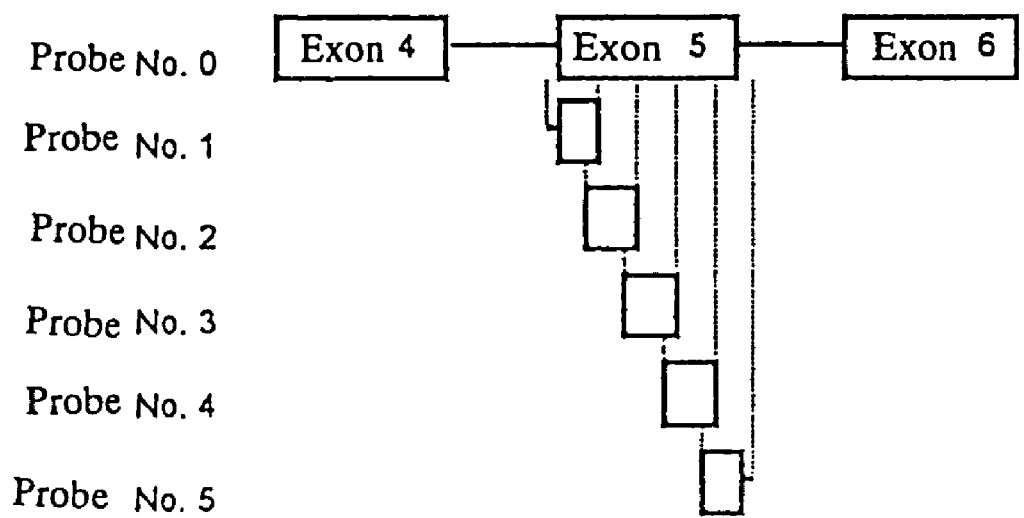
FIG. 4 is a schematic diagram of PS2 pre-mRNA probes. In the figure, six kinds of probes of PS2 pre-mRNA fragment for the binding assay are schematically shown. The region circumscribed with a rectangular frame and the underlined portion each represents exon and intron. All the probes are labeled by in vitro transcription.

In order to detect a PS2 pre-mRNA-binding factor in hypoxia-exposed cells, various $^{35}$S-labeled pre-mRNA probes (RNA probes) shown in FIG. 4 were prepared. By the strategy shown in FIG. 3, a unique pre-mRNA binding assay using the probes as shown in FIG. 4 was established. The results are shown in FIG. 5.

Figure 5:
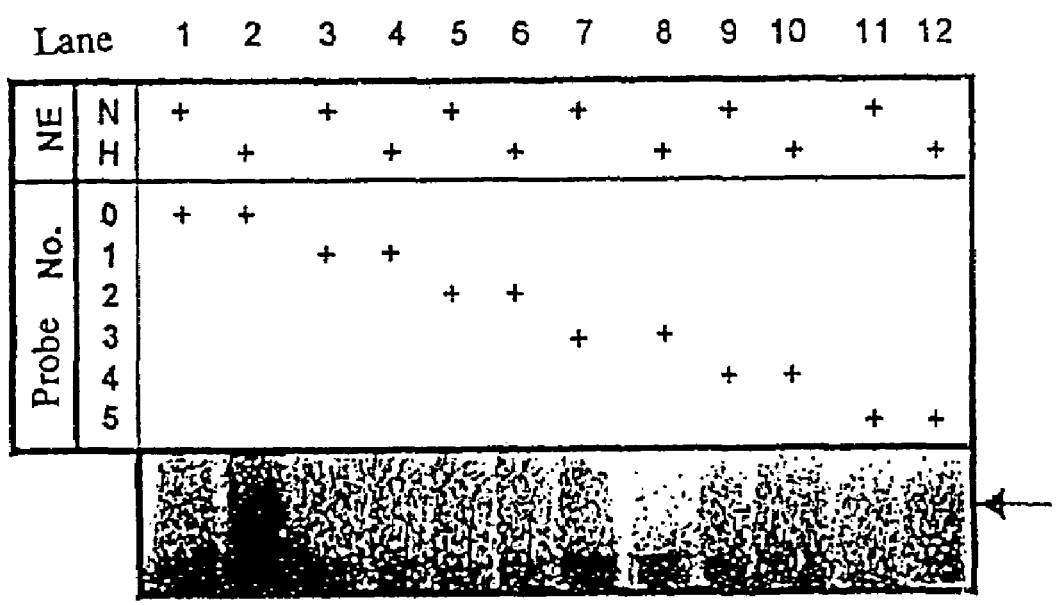
FIG. 5 is a diagram showing the results of a pre-mRNA binding experimental method. SK-N-SH cells were exposed to normoxia or hypoxia, and then collected after 21 hours of stimulation. A nuclear extract from the collected cells was analyzed by the pre-mRNA binding assay using each radioisotope-labeled probe. Next, the nuclear extract was subjected to SDS-PAGE on a polyacrylamide gel on (10 to 20%) concentration gradient and thereafter exposed on an imaging plate for Bas. These experiments were repeated at least four times using different cell cultures, and the same results were obtained.

As a result of the pre-mRNA binding assay using $^{35}$S-labeled probe of No. 0, a signal was not detected at the position of the molecular weight (about 20 kDa) indicated by the black arrow, in the nuclear extract derived from the neuroblastoma SK-N-SH cells under normoxia conditions, as shown in lane 1 in FIG. 5, and in the nuclear extract derived from the neuroblastoma SK-N-SH cells exposed to hypoxic conditions for 21 hours, a signal was detected at the position of the molecular weight (about 20 kDa) indicated by the black arrow, as shown in lane 2 in FIG. 5. Accordingly, it is found that a factor exhibiting PS2 pre-mRNA binding activity is present in the nuclear extract derived from hypoxia-exposed neuroblastoma SK-N-SH cells. By heating the nuclear extract prior to use in pre-mRNA binding assay, the PS2 pre-mRNA binding activity almost disappears, and thus there is a high possibility that this binding activity is derived from a protein but not derived from other factors such as nucleic acid and lipid.

In addition, as shown in lanes 3 to 12 in FIG. 5, it is found that the factor exhibiting PS2 pre-mRNA binding activity, found in the nuclear extract derived from the SK-N-SH cells exposed to hypoxic conditions, binds to the 3'-site of PS2 exon 5.

Further, the influence of each of unlabeled probes of Nos. 1 to 5 on the binding between the probe of No. 0 and the above factor found in the nuclear extract derived from the SK-N-SH cells exposed to hypoxic conditions was examined by pre-mRNA binding assays. The results are shown in FIG. 6.

Figure 6:
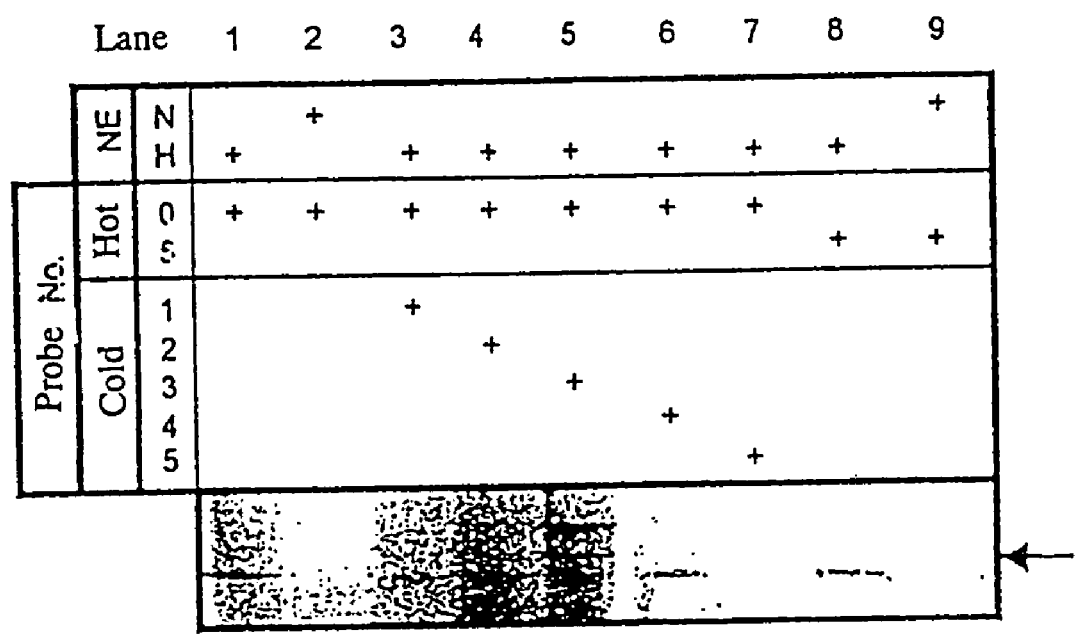
FIG. 6 is a diagram showing the results of the pre-mRNA binding assay. SK-N-SH cells were exposed to normoxia or hypoxia and then collected after 21 hours of stimulation. The nuclear extract was pre-incubated under binding conditions together with each $^{35}$S-unlabeled cold probe. The pre-mRNA binding assay using the pre-incubated reaction solution was initiated by adding each $^{35}$S-labeled hot probe. Next, the mixture was subjected to SDS-PAGE on 15% polyacrylamide gel, followed by exposure to a Bas imaging plate. These experiments were repeated at least four times using different cell cultures, and the same results were obtained.

As shown in FIG. 6, it is found that the binding between the probe of No. 0, and the above factor found in the nuclear extract derived from the hypoxia-exposed SK-N-SH cells is inhibited by addition of $^{35}$S-unlabeled the probe of No. 5, but not inhibited by the other unlabeled probes (Nos. 1 to 4).

Further, the influence of normoxia conditions and hypoxia on induction of the binding activity to the probe of No. 5 in the nuclear extract obtained at different stages after stimulation was examined. As a result, a marked binding activity to the probe of No. 5 under the conditions used was not noted in the nuclear extract derived from the SK-N-SH cells exposed to normoxia conditions. However, the enhancement of the binding activity by hypoxia was noted in the nuclear extract between 16 and 21 hours after stimulation, and persisted for at least 24 hours.

All the experiments in this example were repeated at least 4 times by using other cell cultures, and the same results were obtained. Accordingly, it is suggested that the binding activity induced by hypoxia is specific to the probe of No. 5.

EXAMPLE 3

Purification and Identification of Human PS2 Exon 5-binding Protein

To purify the factor having a binding activity to the probe of No. 5 in Example 2, the fraction to be tested was assayed by adding it to the pre-mRNA-binding reaction product and measuring an increase in the binding activity to the probe of No. 5.

Figure 7:
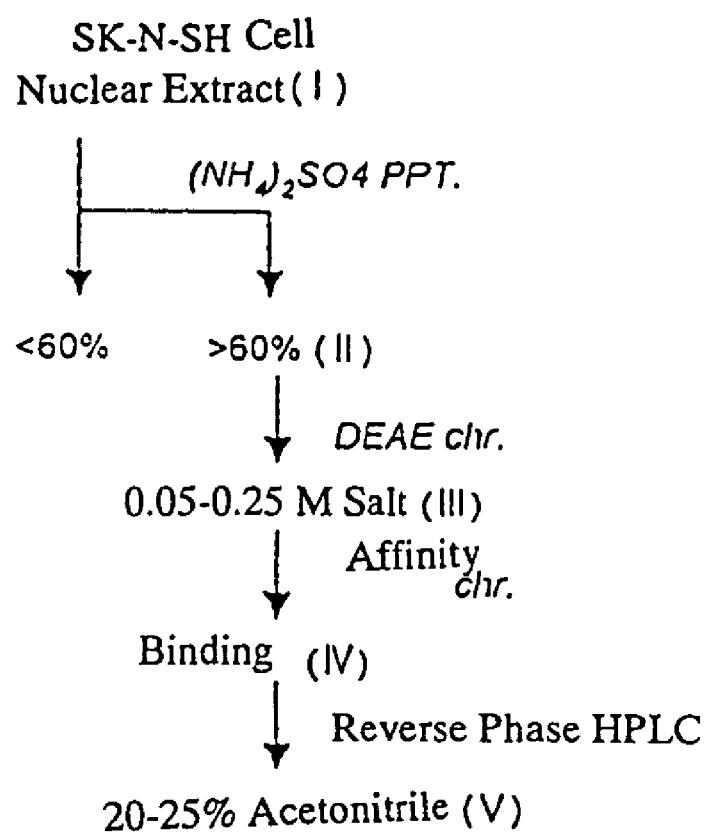
FIG. 7 shows a purification profile of a fraction having a binding activity to Probe No. 5 which is derived from a nuclear extract of human neuroblastoma SK-N-SH cells under hypoxic stress. The purification method is shown in italics. Individual fractions are shown in Roman numerals.

Scheme of purification procedures are shown in FIG. 7. The respective fractions (I) to (V) shown in FIG. 7 were assayed by silver staining (FIG. 8) and RNA binding assays (FIG. 9).

The nuclear extract (FIG. 9, lane 1) derived from SK-N-SR cells exposed to hypoxic conditions in the same manner as in Example 1 was fractionated with 60% saturated ammonium sulfate, to give a fraction as a supernatant having a binding activity to the RNA probe of No. 5 [fraction (II), FIG. 7 (II)]. The result of silver staining of the above fraction (II) is shown in lane 2 in FIG. 8, and the result of RNA binding assay is shown in lane 2 in FIG. 9.

The above fraction (II) was dialyzed twice against 5 L of 50 mM Tris-HCl buffer (pH 7.5) at 4° C. for 4 hours, thereby removing ammonium sulfate. The resulting dialysate was subjected to anion-exchange chromatography on DEAE column (manufactured by Pharmacia Biotech), and then the column was washed with 10 ml of 50 mM Tris-HCl buffer (pH 7.5). Then, the elution was carried out by using 10 ml of 50 mM Tris-HCl buffer (pH 7.5) containing 1 M NaCl, to give a fraction [fraction (III), FIG. 7 (III)] having a potent binding activity to the RNA probe of No. 5. The result of silver staining of the above fraction (III) is shown in lane 3 in FIG. 8, and the result of RNA binding assay thereof is shown in lane 3 in FIG. 9.

The above fraction (III) was dialyzed twice against 5 L of 50 mM Tris-HCl buffer (pH 7.5) at 4° C. for 4 hours. Then, the resulting dialysate was applied to 5'-amino-2'-O-methyl oligo RNA (5'-aucuucuugguggugcucuacaaguac-cgcugcuacaaggugaggcccu-3', SEQ ID NO: 24)-coupled CNBr-activated Sepharose 4B (manufactured by Pharmacia Biotech) affinity column. The above affinity column was washed with 10 ml of the above incubation buffer and then eluted with 15 ml of the incubation buffer containing 1 M NaCl to give a fraction having a binding activity to the RNA probe of No. 5 [fraction (IV), FIG. 7 (IV)] (FIG. 9, lane 4). The result of silver staining of fraction (IV) is shown in lane 4 in FIG. 8, and the result of RNA binding assay thereof is shown in lane 4 in FIG. 9.

Figure 8:
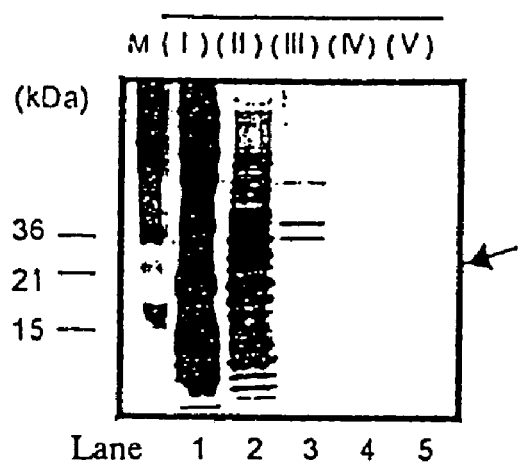
FIG. 8 is a diagram showing the results of analysis of proteins (25 μl/fraction) in each purification stage shown in FIG. 7 by 15% SDS-PAGE and silver staining. In the figure, M is a molecular weight (kDa) marker.
Figure 9:
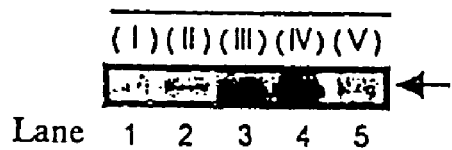
FIG. 9 is a diagram showing the binding activity of $^{35}$S-labeled Probe No. 5 to a fraction (15 μl/fraction) in each purification stage.

From the result of silver staining, it was found that the fraction was not completely purified, as shown in lane 4 in FIG. 8.

Then, the above fraction (IV) was dialyzed twice against 5 L of Mili-Q water at 4° C. for 4 hours. The resulting dialysate was completely lyophilized and then redissolved in Mili-Q water containing 0.1% TFA.

The resulting solution was subjected to reverse-phase chromatography on Waters 5C18-MS (4.6 mm×150 mm) column. Specifically, the column was washed with Mili-Q water containing 0.1% TFA. Thereafter, the elution was carried out by using a linear gradient of 0 to 100% acetonitrile in 25 ml Mili-Q water containing 0.1% TFA, followed by 5 ml of 100% acetonitrile containing 0.1% TFA.

As a result, a fraction showing a single peak eluted with 20 to 25% acetonitrile [fraction (V), FIG. 7(V)] was obtained. This fraction showed a single band at the molecular weight indicated by the black arrow, as shown in lane 5 in FIG. 8, by silver staining after SDS-PAGE. However, the binding activity of the final fraction was dramatically reduced as compared in the previous step [FIG. 7 (IV)]. When the final concentration of acetonitrile in the binding reaction solution was adjusted to 30% by weight, the binding activity of the original fraction to the probe of No. 5 was completely lost, and thus it is found that the reduction in the binding activity of the final fraction depends on acetonitrile contained in the elution buffer for reverse-phase chromatography.

The resulting fraction was separated by electrophoresis on 12% polyacrylamide gel containing 0.1% SDS at a constant current of 15 mA/plate for 2 hours at room temperature. Thereafter, a gel section containing the separated protein band was cut out, and the protein was digested in gel with trypsin. The eluted peptide fragment was separated by HPLC with TSK gel ODS-80Ts QA column (2.0 mm×250 mm, manufactured by Tosoh). Then, the separated peptide fragment was analyzed with an automated protein sequencer (HP G1005A Protein Sequencing System). The obtained information on the peptide sequence was used for searching data bases.

The single band in the final fraction was analyzed for its peptide sequence, to give 17 amino acid sequences. The obtained peptide sequence was compared with known proteins in a sequence data base, and as a result, PS2 pre-mRNA-binding protein in the nuclear extract derived from hypoxia-exposed SK-N-SH cells matched completely with HMG-I (GenBank Accession No. P17096).

EXAMPLE 4

Evaluation of Binding Activity of HMG-I

To confirm that HMG-I actually has a binding activity on the basis of the results in Example 3, an antibody against HMG-I protein and the nuclear extract derived from hypoxia-exposed SK-N-SH cells or the nuclear extract derived from SK-N-SH cells under normoxia conditions were used in supershift assays according to Experimental Example 13, as follows.

Specifically, the nuclear extract of an amount equivalent to 5 μg of protein was pretreated by incubation at 4° C. for 8 hours with 0.5 to 2.0 μg anti-HMG-I/Y antibody (manufactured by Santa Cruz Biotechnology). The pretreated nuclear extract was incubated with 10 μg tRNA in the incubation buffer, and then a total volume of 50 μL of $^{32}$P-labeled RNA probe [1 μg, the probe of No. 5 shown in FIG. 4] was added to the resulting product and incubated at 25° C. for 30 minutes. The bound probe was separated from the free probe by electrophoresis at a constant voltage of 11 V/cm for 1.5 hours at 4° C. on 4% polyacrylamide gel in a buffer (pH 8.5) containing 50 mM Tris, 0.38 M glycine and 2 mM EDTA. The gel was fixed and dried. Then, the dried gel was exposed to an X-ray film, thereby performing to autoradiography.

Figure 10:
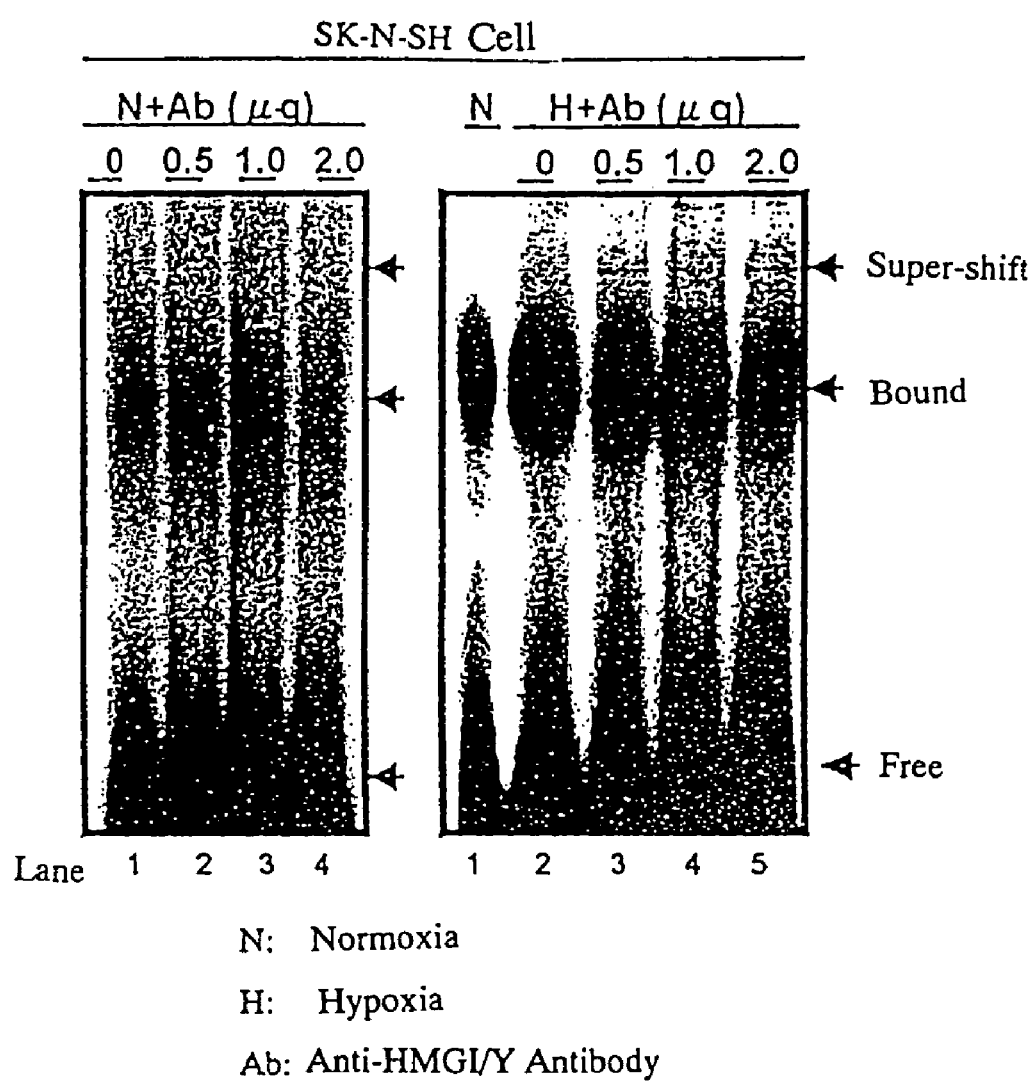
FIG. 10 is a diagram showing the results of super shift assay using an antibody against HMG-I/Y protein. SK-N-SH cells were collected after 21 hours of normoxia (left) or hypoxic (right) stimulation. Prior to the reaction with the radioisotope-labeled Probe No. 5, the nuclear extract was incubated in a usual buffer in the presence or absence of the antibody against the HMG-I/Y protein. Next, the sample was subjected to gel retardation electrophoresis and autoradiography. These experiments were repeated at least four times using different cell cultures, and the same results were obtained.

As a result, the nuclear extract derived from hypoxia-exposed SK-N-SH cells showed more potent binding activity than that of the nuclear extract derived from SK-N-SH cells under normoxia conditions, as shown in lanes 1 and 2 in the right panel in FIG. 10. In addition, it is found that by the pretreatment with the anti-HMG-I/Y antibody, this increase in the binding activity was super-shifted in an antibody concentration-dependent manner, as shown in lanes 3 to 5 in the right panel in FIG. 10. However, the nuclear extract derived from SK-N-SH cells under normoxia conditions in the control experiment did not show a significant effect attributable to addition of the HMG-I/Y antibody, as shown in the left panel in FIG. 10.

From these results, it is revealed that the substance having a binding activity to the probe of No. 5, derived from hypoxia-exposed SK-N-SH cells, is HMG-I.

Further, it is revealed that in the hypoxia-exposed cells, the binding activity of HMG-I protein to the probe of No. 5 does not depend on UV irradiation in the pre-mRNA binding assay.

EXAMPLE 5

Determination of PS2 Pre-mRNA Binding Site

Figure 11:
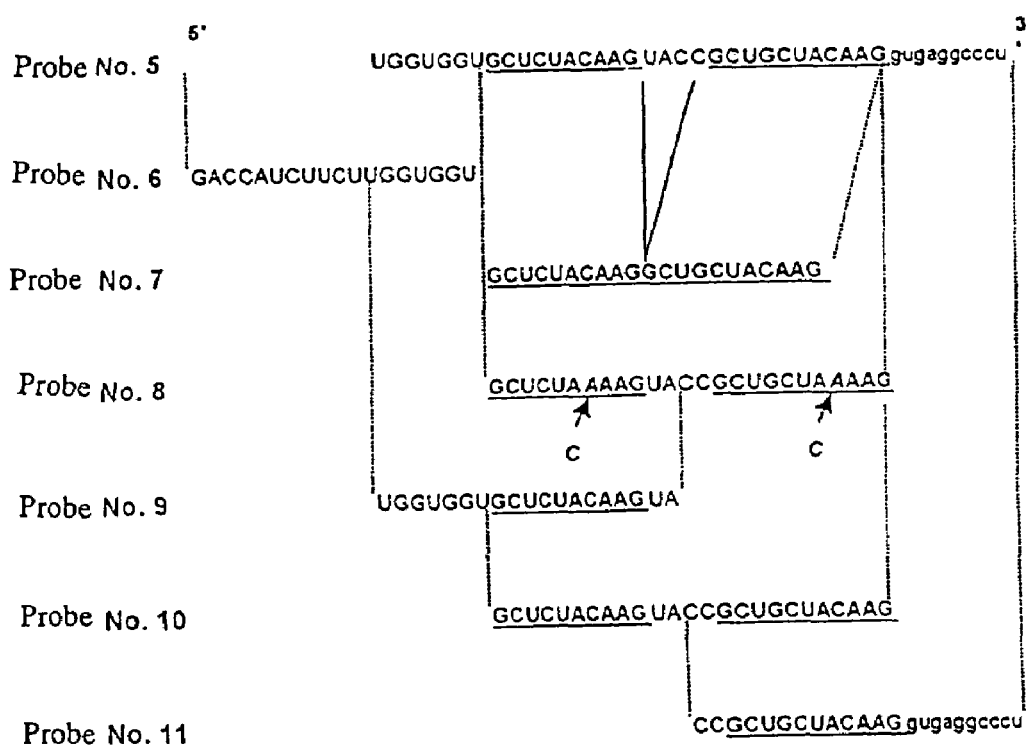
FIG. 11 is a diagram showing seven kinds of structures of PS2 pre-mRNA.
Probe No. 5 (SEQ ID NO: 3)
Probe No. 6 (SEQ ID NO: 25)
Probe No. 7 (SEQ ID NO: 4)
Probe No. 8 (SEQ ID NO: 69)
Probe No. 9 (SEQ ID NO: 5)
Probe No. 10 (SEQ ID NO: 6)
Probe No. 11 (SEQ ID NO: 7)

The present inventors directed to their attention to two repeated analogous sequences (repeated sequences) at the 3'-terminal of PS2 exon 5 for the probe of No. 5 in FIG. 4, and estimated that HMG-I protein bind to these repeated sequences. Accordingly, six RNA probes (the probes of Nos. 6 to 11) shown in FIG. 11 were prepared as derivatives of the probe of No. 5, and the resulting probes were used in pre-mRNA binding assays according to the above Experimental Example 7. The results are shown in FIG. 12. The above repeated sequences are the underlined sequences in the probe of No. 5 in FIG. 11, and shown in SEQ ID NOs: 1 and 2, respectively.

As shown in lane 1 in FIG. 12, the binding activity to the probe of No. 5 could not be detected in the nuclear extract derived from SK-N-SH cells exposed to normoxia conditions. On the other hand, it was found that in the nuclear extract derived from hypoxia-exposed SK-N-SH cells, the binding activity to the probe of No. 5 was strongly increased at the position of the molecular weight indicated by the black arrow, as shown in lane 2 in FIG. 12 similar to those in FIGS. 5 and 6.

However, as shown in lane 3 in FIG. 12, this increase in the binding activity by exposure to hypoxia disappeared by using a probe (the probe of No. 6 in FIG. 11) lacking the sequences of SEQ ID NOs: 1 and 2. In the nuclear extract derived from hypoxia-exposed SK-N-SH cells, however, the binding was significantly increased (FIG. 12, lane 4) by using the probe of No. 7 (FIG. 11) containing SEQ ID NOs: 1 and 2 bound directly thereto. Further, when the probe of No. 8 (FIG. 11) containing those sequences of SEQ ID NOs: 1 and 2 wherein C was replaced by A, the binding activity disappeared completely in almost all the regions as shown in lane 5 in FIG. 12. Further, when the binding activity was observed by using either of SEQ ID NO: 1 or 2 in the binding assay (FIG. 12, lanes 6 and 8), the binding activity to the probe of No. 10 having both the sequences was the highest (FIG. 12, line 7). These results mean that either one or both of SEQ ID NOs: 1 and 2 are necessary for the binding activity of HMG-I protein to PS2 pre-mRNA.

FIG. 12 shows that either one or both of SEQ ID NOs: 1 and 2 are necessary for the binding activity of HMG-I to PS2 pre-mRNA. When the above sequences of SEQ ID NO: 1 and SEQ ID NO: 2 were examined for homology in comparison with other genes in data bases, it is revealed that the above SEQ ID NOs: 1 and 2 are sequences unique to PS2 exon 5.

The above results show that the HMG-I/Y protein binds to a single-stranded RNA, and the HMG-I protein recognizes and binds to a site consisting of a sequence comprising gcucuacaag (SEQ ID NO: 1) and/or gcugcuacaag (SEQ ID NO: 2).

EXAMPLE 6

Influence of Hypoxia on Expression of HMG-I mRNA and Immunoreactive HMG-I Protein To determine whether or not the increase in the binding activity depends on an increase in expression of HMG-I, the expression levels of HMG-I mRNA and the protein under normoxia conditions was compared with those upon exposure to hypoxia.

As shown in the upper left panel in FIG. 13, it is revealed by Northern blot analysis that the HMG-I mRNA level is dramatically increased by exposure to hypoxia which is the condition for expressing PS2V in the neuroblastoma SK-N-SH cells. However, when hypoxia-exposed HEK-293T cells not inducing PS2V were used (FIG. 13, the upper middle panel) or tunicamycin-treated SK-N-SH cells not inducing PS2V were used (FIG. 13, the upper middle panel), no significant increase was observed under stress.

As a result, as indicated by the upper arrow in the left panel in FIG. 14, it is found by immunoblot analysis with the anti-HMG-I/Y antibody that the immunoreactive HMG-I protein was expressed at higher levels in the nuclear extract of hypoxia-exposed SK-N-SH cells than in the extract of the cells under normoxia conditions. However, it is found that in the nuclear extract derived from SK-N-SH cells, the immunoreactive HMGY protein does not undergo the effect of hypoxic stress, as indicated by the lower arrow in the left panel in FIG. 14. As shown in the right panel in FIG. 14, it is found that no significant immunoreactivity with anti-HMG-I/Y antibody is observed in the hypoxia-exposed HEK-293T cells.

The results shown in the experiment using hypoxia-exposed HEK-293T cells and tunicamycin-treated SK-N-SH cells are contradictory to those of a previous report showing that the cells with HMG-I/Y mRNA in a steady state are first increased due to hypoxia, resulting in an increase in HMG-I/Y protein [Ji, Y. S. et al., Circ. Res., 83, 295-304 (1998)]. This evident contradiction may reflect a difference among the respective cell lines.

EXAMPLE 7

Localization of HMG-I Protein at the Cellular Level

To examine the localization of the protein in the cells, the SK-N-SH cell culture was exposed to hypoxic conditions for 21 hours, and the HMG-I protein was detected under an immunofluorescence microscope by using an anti-HMG-I/Y antibody and anti-SC35 antibody. The above anti-SC35 antibody is an antibody against SC35 protein, a factor essential for splicing. In this example, an immunocytochemistry was carried out using the above anti-SC35 antibody as a maker for a speckle where a splicing factor is present.

It is found in the immunocytochemistry that, as shown in normoxia conditions in FIG. 15, the HMG-I protein was mainly localized in the nuclei in the cells under normoxia conditions, and weak and scattering immunoreactions were obtained in the cytoplasm without co-localizing with the immunoreactive SC35 protein occurring only in the nuclear speckle.

In the nuclear speckle where SC35 was co-localized, however, more potent immunoreactivity was obtained, and the immunoreactivity in the cytoplasm in the hypoxia-exposed SK-N-SH cells was lower than in the cells under normoxia conditions. Accordingly, the HMG-1 protein is not only induced in the SK-N-SH cells by hypoxic stimulation but also accumulated from the cytoplasm to the nuclei, and there would be a correlation between expression of HMG-I and induction of PS2V.

EXAMPLE 8

In Vivo Effect of Transient Transfection with HMG-I and HMG-Y on PS2 Gene Exon 5 Skipping According to the above literature by Sato et al. [Sato et al., J. Neurochem., 72, 2498-2505 (1999)], alternatively spliced form PS2 gene lacking exon 5 was obtained from a brain affected with sporadic Alzheimer's disease and a hypoxia-exposed SK-N-SH cell respectively.

To determine whether or not alternative splicing accompanied by lack of defection in PS2 gene exon 5 was caused by HMG-I/Y, the effect of the transient expression of HMG-I on induction of PS2V in SK-N-SH cultured cells and HEK-293T cultured cells was examined. The results of immunoblot analysis are shown in FIG. 16, and the results of RT-PCR are shown in FIG. 17.

As shown in FIG. 16, it was found that the nuclear extract derived from HMG-I-transfected SK-N-SH cells and the nuclear extract derived from HMG-I-transfected HEK-293T cells had expressed HMG-I protein having more potent immunoreactivity than in the nuclear extract derived from mock-transfected cells. Further, it is found that in RT-PCR assay of the total RNA derived from mock-transfected SK-N-SH cells, the full-length PS2 gene was detected as the major transcription product (PS2 in FIG. 17) at the position of its corresponding molecular weight, as shown in lane 1 in FIG. 17. In contrast, when the total RNA derived from HMG-I-transfected cells was used, it was found by RT-PCR assay that not only the full-length PS2 as the major transcription product (PS2 in FIG. 17) but also a shorter chain RT-PCR product (PS2V in FIG. 17) was detected in a manner which depends on the amount of HMG-I, as shown in lanes 2 and 3 in FIG. 17.

By direct sequence analysis, it is revealed that the abnormal RT-PCR product is an alternative splicing product of PS2 lacking exon 5. On the other hand, weak induction of PS2V is observed in SK-N-SH cells upon the transient transfection of HMG-Y, but the HMGY protein is not induced by hypoxia in the nuclear extract derived from SK-N-SH cells, as shown in lanes 4 and 5 in FIG. 17. Further, in the HEK-293T cell which is a cell line wherein PS2V is not induced by hypoxia (FIG. 2), PS2V is detected due to overexpression of HMG-I, as shown in FIG. 17.

It is known that U1 (70 K) snRNP, an essential factor for splicing, usually binds to a 5'-splicing site. Accordingly, it is expected that HMG-I can inhibit the binding of U1 snRNP to pre-mRNA. Hence, the effect of HMG-I on the binding activity of U1 (70K) snRNP to pre-mRNA in the nuclear extract derived from SK-N-SH cells was examined.

Using an antibody against U1 (70 K) snRNP [anti-U1 (70 K) snRNP antibody manufactured by Santa Cruz Biotechnology], supershift assay was carried out according to Experimental Example 13, as follows.

Specifically, the nuclear extract of an amount equivalent to 5 μg of protein was pretreated by incubation at 4° C. for 8 hours with 1 μg anti-HMG-I/Y antibody (manufactured by Santa Cruz Biotechnology). The resulting pretreated product was incubated with 2 μg tRNA in an incubation buffer [composition: 12 mM HEPES-NaOH buffer (pH 7.9) containing 60 mM KCl, 4 mM MgCl$_2$, 1 mM EDTA, 1 mM EGTA, 1 mM DTT, 10% glycerol and 1 mM PMSF]. Then, $^{32}$P-labeled RNA probe [1 μg, the probe of No. 5 shown in FIG. 4] was added thereto and incubated at 25° C. for 30 minutes (total volume: 50 μl). The resulting reaction product was electrophoresed at a constant voltage of 11 V/cm for 1.5 hours at 4° C. on 4% polyacrylamide gel in a buffer (pH 8.5) containing 50 mM Tris, 0.38 M glycine and 2 mM EDTA, whereby the bound probe was separated from the free probe. The gel after electrophoresis was fixed, dried and exposed to an X-ray film. The results are shown in FIG. 18.

As shown in the left panel in FIG. 18, it is found that by the pretreatment with the anti-U1 (70 K) snRNP antibody, the binding activity to the probe of No. 12 in the nuclear extract derived from Mock-transfected SK-N-SH cells was super-shifted in an antibody-concentration dependent manner. In addition, as shown in lane 1 in the left panel and lane 1 in the right panel in FIG. 18, more potent binding activity is observed in the nuclear extract derived from HMG-I-transfected SK-N-SH cells than in the nuclear extract derived from Mock-transfected cells.

However, the binding activity in the nuclear extract from HMG-I-transfected SK-N-SH cells was not affected by addition of the anti-U1 (70 K) snRNP antibody, as shown in lanes 2 to 4 in the right panel in FIG. 18. Namely, these results indicate that HMG-I inhibits the activity of U1 (70 K) snRNP to bind to pre-mRNA.

Further, the results of determining the inhibitory effect of HMG-I on the binding activity of U1 (70 K) snRNP to pre-mRNA are shown in FIG. 19.

As shown in FIG. 19, it is found that HMG-I binds directly to U1 (70 K) snRNP in the nuclear extract derived from hypoxia-exposed SK-N-SH cells, but does not bind to U1 (70 K) snRNP in the nuclear extract derived from the cells exposed to normoxia conditions.

The transient transfection of HMG-I in SK-N-SH cells induced expression of PS2V (FIG. 17). Further, detectable PS2V was observed (FIG. 17) by overexpression of HMG-I in the HEK-293T cell line which is a cell line not expressing PS2V (FIG. 2) by exposure to hypoxia. Accordingly, it can be said that PS2V is induced by merely overexpressing HMG-I in the cells. It is suggested that an increase in the expression of HMG-I is necessary rather than stimulation with hypoxia in order to induce PS2V.

U1 (70 K) snRNP is an essential factor for splicing, and recognizes a 5'-splicing site and binds to the 5'-splicing site. U1 (70 K) snRNP recognition sequence and HMG-I recognition sequence are close to each other on the probe of No. 5. The binding activity of U1 (70 K) snRNP to PS2 mRNA was inhibited in vitro in the nuclear extract derived from HMG-I-transfected SK-N-SH (FIG. 18).

Further, the HMG-I protein bound to U1 (70 K) snRNP in the nuclear extract derived from hypoxia-exposed SK-N-SH cells (FIG. 19). It is presumed that the association between HMG-I and U1 (70 K) snRNP observed in this example inhibits the binding of SF2/ASF to U1 (70 K) snRNP, resulting in inhibition of the binding activity of U1 (70 K) snRNP to pre-mRNA.

In addition, there is suggested a possibility that HMG-I inhibits the binding of U1 (70 K) snRNP to pre-mRNA or another splicing factor as shown in FIG. 20, thereby inhibiting the action of U1 (70 K) snRNP on PS2 pre-mRNA.

EXAMPLE 9

Expression of HMG-I/Y Protein in sAD Brain

It is presumed that if HMG-I protein actually induces alternative splicing of PS2 lacking exon 5, higher expression of HMG-I must be observed in a sAD brain than in a control brain. Accordingly, the expression level of HMG-I in the control brain was compared with that of the sAD brain by immunoblot assays. The results are shown in FIG. 21.

As shown in the left and right panels in FIG. 21, both HMG-I protein and HMG-Y protein are increased as compared with those in the age-matched control, and expressed in the whole lysate and nuclear fraction derived from the hippocampuses of three different sAD patients. In the cytosol fraction of hippocampus, however, there is no significant difference between the sAD patients and the control, as shown in the middle panel in FIG. 21.

To specify the HMG-I/Y-expressing region in the hippocampus, immunohistochemical analysis was carried out using an anti-HMG-I/Y antibody. The results are shown in FIG. 22. As shown in FIG. 22, a higher exhibition of immunoreactivity is recognized in a pyramidal cell layer in the hippocampus CA1 region of the sAD brain than in the control.

In immunohistochemical analysis, the immunoreactive HMG-I/Y protein was detected in the nuclear fraction derived from the hippocampus of the control brain (FIG. 21), but substantially no HMG-I/Y protein was detected in the hippocampal CA1 region of the control brain (FIG. 22). This is because HMG-I/Y was expressed in a region of hippocampal stratum lacunosum-moleculare of the control, and there was no difference as compared with the sAD brain.

More potent expression of both HMG-I protein and HMG-Y protein was observed in the nuclear fraction of the hippocampus of the sAD brain than in the control, but not observed in the cytosol fraction (FIG. 21). Also, by immunohistological assay, the HMG-I/Y protein was detected in pyramidal cells in the hippocampus CA1 region of the sAD brain (FIG. 22). These results show a possibility that the HMG-I/Y protein binds to PS2 pre-mRNA, to actually induce a splicing variant of PS2 gene lacking exon 5 in the brain and the cell line with sAD.

EXAMPLE 10

Screening of Inhibitor of Binding Between Presenilin-2 Gene Exon 5 and HMG-I Protein A chemical library, antisense nucleic acids designed on the basis of the nucleotide sequence of SEQ ID NO: 1 and/or the nucleotide sequence of SEQ ID NO: 2, and derivatives thereof are used as test substances.

In the presence or absence of the above test substances, the binding between a $^{35}$S-labeled RNA probe containing the nucleotide sequence as shown in SEQ ID NO: 1 and the nucleotide sequence as shown in SEQ ID NO: 2 and the HMG-I protein is examined by the same technique as in the pre-mRNA binding assay in the above Experimental Example 7.

When a signal attributable to a complex formed by binding of the $^{35}$S-labeled RNA probe to the HMG-I protein is detected in the absence of the test substance but the signal is not detected in the presence of the test substance, the test substance can be a candidate substance of an inhibitor of the binding.

EXAMPLE 11

A nucleotide sequence of the HMG-I recognition motif was determined by in vitro DNA screening assay. The procedure of the in vitro DNA screening assay is as follows: a synthetic DNA [5'-GGTGATCAGATTCTGATCCA(N$_{31}$) TGAAGCTTGGATCCGTCGC-3' (SEQ ID NO: 65)] containing a random sequence of 31 nucleotides (20.7% A, 22.7% C, 31.5% T and 25.1% G as determined by direct sequencing of 16 clones) was amplified by using

```
                                              (SEQ ID NO:67)
5'-GTAATACGACTCACTATAGGGTGATCAGATTCTGATCCA-3'
and (SEQ ID NO:67)
5'-GCGACGGATCCAAGCTTCA-3'
``` as primers in PCR of 7 cycles, wherein one cycle consists of reactions at 94° C. for 1 minute/53° C. for 1 minute/72° C. for 1 minute.

The resulting product was incubated with *E. coli* expression recombinant HMG-I (referred to as rHMG-I) in an incubation buffer (12 mM HEPES-NaOH (pH 7.9) containing 60 mM KCl, 4 mM MgCl$_2$, 1 mM EDTA, 1 mM EGTA, 1 mM DTF, 10% glycerol and 1 mM PMSF) at 25° C. for 30 minutes.

The resulting reaction solution was subjected to immunoprecipitation with an antibody against HMG-I. PCR of 7 cycles wherein one cycle consists of reactions at 94° C. for 1 minute/53° C. for 1 minute/72° C. for 1 minute were carried out using the immunoprecipitated product as the template and

```
                                              (SEQ ID NO:67)
5'-GTAATACGACTCACTATAGGGTGATCAGATTCTGATCCA-3'
and (SEQ ID NO:68)
5'-GCGACGGATCCAAGCTTCA-3'
``` as the primers. The resulting PCR product was cloned into pGEM-T vector (manufactured by Promega) and analyzed by direct sequencing.

As a result, it was suggested that a consensus sequence as shown in the highest position in FIG. 24 is the HMG-I recognition motif.

Then, the action of 2'-O-methyl oligo RNA (SEQ ID NO: 27) on the binding of a $^{32}$P-labeled DNA probe [gcgG(A)GT(A)A(T)ATTTcgc (SEQ ID NO: 66)] containing the above HMG-I recognition motif to HMG-I was examined.

After the protein content of the nuclear extract was measured, each of extracts of an amount equivalent to 5 μg of protein, 1 μg poly dIdC, and 2'-O-methyl oligo RNA (SEQ ID NO: 27) at various concentrations were added to the above incubation buffer, and then 1 μg $^{32}$P-labeled DNA probe [gcgG(A)GT(A)A(T)ATTTcgc (SEQ ID NO: 66)] was added thereto to form 50 μl solution which was then incubated at 25° C. for 30 minutes.

Thereafter, the reaction solution was electrophoresed for 1.5 hours at 4° C. at a constant voltage of 11 V/cm on 4% polyacrylamide gel in a buffer containing 50 mM Tris, 0.38 M glycine and 2 mM EDTA, whereby the bound probe was separated from the free probe. After electrophoresis, the gel was dried and analyzed by autoradiography.

As a result, the binding between the $^{32}$P-labeled DNA probe containing the above HMG-I recognition motif and HMG-I was dramatically increased by overexpression of HMG-I in SK-N-SH cells, as shown in lanes 1 and 2 in panels A and B in FIG. 25.

However, as shown in lanes 3 and 4 in panels A and B in FIG. 25, no significant influence of the above 2'-O-methyl oligo RNA on the increase in the activity of HMG-I to the above DNA probe was observed.

Accordingly, the inhibitory action of the above 2'-O-methyl oligo RNA is specific to the binding of HMG-I to RNA, but not specific to the binding of HMG-I to DNA.

Sequence Listing Free Text

SEQ ID NO: 1 shows a sequence of a binding region.
SEQ ID NO: 2 shows a sequence of a binding region.
SEQ ID NO: 3 shows a sequence of RNA probe No. 5.
SEQ ID NO: 4 shows a sequence of RNA probe No. 7.
SEQ ID NO: 5 shows a sequence of RNA probe No. 9.
SEQ ID NO: 6 shows a sequence of RNA probe No. 10.
SEQ ID NO: 7 shows a sequence of RNA probe No. 11.
SEQ ID NO: 8 shows a sequence of RNA probe No. 8.
SEQ ID NO: 9 shows a sequence of primer ps251.
SEQ ID NO: 10 shows a sequence of primer ps231.
SEQ ID NO: 11 shows a sequence of primer ps252.
SEQ ID NO: 12 shows a sequence of primer ps233.
SEQ ID NO: 13 shows a sequence of DNA probe No. 1.
SEQ ID NO: 14 shows a sequence of DNA probe No. 2.
SEQ ID NO: 15 shows a sequence of DNA probe No. 3.
SEQ ID NO: 16 shows a sequence of DNA probe No. 4.
SEQ ID NO: 17 shows a sequence of DNA probe No. 5.
SEQ ID NO: 18 shows a sequence of DNA probe No. 6.
SEQ ID NO: 19 shows a sequence of DNA probe No. 7.
SEQ ID NO: 20 shows a sequence of DNA probe No. 8.
SEQ ID NO: 21 shows a sequence of DNA probe No. 9.
SEQ ID NO: 22 shows a sequence of DNA probe No. 10.
SEQ ID NO: 23 shows a sequence of DNA probe No. 11.
SEQ ID NO: 24 shows a sequence of 5'-amino-2'-O-methyl oligo RNA used as a ligand in an affinity column.
SEQ ID NO: 25 shows a sequence of RNA probe No. 6.
SEQ ID NO: 26 shows a sequence of RNA probe No. 12.
SEQ ID NO: 28 shows a sequence of a synthetic DNA containing the HMG-I recognition motif.
SEQ ID NO: 29 shows a sequence of a synthetic DNA containing the HMG-I recognition motif.
SEQ ID NO: 30 shows a sequence of a synthetic DNA containing the HMG-I recognition motif.
SEQ ID NO: 31 shows a sequence of a synthetic DNA containing the HMG-I recognition motif.
SEQ ID NO: 32 shows a sequence of a synthetic DNA containing the HMG-I recognition motif.
SEQ ID NO: 33 shows a sequence of a synthetic DNA containing the HMG-I recognition motif.
SEQ ID NO: 34 shows a sequence of a synthetic DNA containing the HMG-I recognition motif.
SEQ ID NO: 35 shows a sequence of a synthetic DNA containing the HMG-I recognition motif.

SEQ ID NO: 36 shows a sequence of a synthetic DNA containing the HMG-I recognition motif.

SEQ ID NO: 37 shows a sequence of a synthetic DNA containing the HMG-I recognition motif.

SEQ ID NO: 38 shows a sequence of a synthetic DNA containing the HMG-I recognition motif.

SEQ ID NO: 39 shows a sequence of a synthetic DNA containing the HMG-I recognition motif.

SEQ ID NO: 40 shows a sequence of a synthetic DNA containing the HMG-I recognition motif.

SEQ ID NO: 41 shows a sequence of a synthetic DNA containing the HMG-I recognition motif.

SEQ ID NO: 42 shows a sequence of a synthetic DNA containing the HMG-I recognition motif.

SEQ ID NO: 43 shows a sequence of a synthetic DNA containing the HMG-I recognition motif.

SEQ ID NO: 44 shows a sequence of a synthetic DNA containing the HMG-I recognition motif.

SEQ ID NO: 45 shows a sequence of a synthetic DNA containing the HMG-I recognition motif.

SEQ ID NO: 46 shows a sequence of a synthetic DNA containing the HMG-I recognition motif.

SEQ ID NO: 47 shows a sequence of a synthetic DNA containing the HMG-I recognition motif.

SEQ ID NO: 48 shows a sequence of a synthetic DNA containing the HMG-I recognition motif.

SEQ ID NO: 49 shows a sequence of a synthetic DNA containing the HMG-I recognition motif.

SEQ ID NO: 50 shows a sequence of a synthetic DNA containing the HMG-I recognition motif.

SEQ ID NO: 51 shows a sequence of a synthetic DNA containing the HMG-I recognition motif.

SEQ ID NO: 52 shows a sequence of a synthetic DNA containing the HMG-I recognition motif.

SEQ ID NO: 53 shows a sequence of a synthetic DNA containing the HMG-I recognition motif.

SEQ ID NO: 54 shows a sequence of a synthetic DNA containing the HMG-I recognition motif.

SEQ ID NO: 55 shows a sequence of a synthetic DNA containing the HMG-I recognition motif.

SEQ ID NO: 56 shows a sequence of a synthetic DNA containing the HMG-I recognition motif.

SEQ ID NO: 57 shows a sequence of a synthetic DNA containing the HMG-I recognition motif.

SEQ ID NO: 58 shows a sequence of a synthetic DNA containing the HMG-I recognition motif.

SEQ ID NO: 59 shows a sequence of a synthetic DNA containing the HMG-I recognition motif.

SEQ ID NO: 60 shows a sequence of a synthetic DNA containing the HMG-I recognition motif.

SEQ ID NO: 61 shows a sequence of a synthetic DNA containing the HMG-I recognition motif.

SEQ ID NO: 62 shows a sequence of a synthetic DNA containing the HMG-I recognition motif.

SEQ ID NO: 63 shows a sequence of a synthetic DNA containing the HMG-I recognition motif.

SEQ ID NO: 64 shows a sequence of a synthetic DNA containing the HMG-I recognition motif.

SEQ ID NO: 65 shows a sequence of a synthetic DNA used in an in vitro DNA screening assay. n represents G, A, T or C.

SEQ ID NO: 66 shows a sequence of a synthetic DNA containing the HMG-I recognition motif.

SEQ ID NO: 67 shows a sequence of a primer used in an in vitro DNA screening assay.

SEQ ID NO: 68 shows a sequence of a primer used in an in vitro DNA screening assay.

INDUSTRIAL APPLICABILITY

According to the present invention, there can be provided an element that can be associated with the generation of PS2V. According to the nucleic acid of the present invention, there are exhibited some excellent characteristics that the nucleic acid can be a target for treatment and/or prevention of a disease caused by aberrant splicing, a neurodegenerative disease represented by Alzheimer's disease, or the like. In addition, according to the method for screening an inhibitor that can inhibit the generation of PS2V of the present invention, there can be provided an inhibitor for inhibiting a binding between protein-nucleic acid caused by aberrant splicing.

SEQUENCE LISTING

```
<160> NUMBER OF SEQ ID NOS: 68

<210> SEQ ID NO 1
<211> LENGTH: 10
<212> TYPE: RNA
<213> ORGANISM: Artificial Sequence
<220> FEATURE:
<223> OTHER INFORMATION: Description of Artificial Sequence: a sequence
      of binding region

<400> SEQUENCE: 1
gcucuacaag                                                              10

<210> SEQ ID NO 2
<211> LENGTH: 11
<212> TYPE: RNA
<213> ORGANISM: Artificial Sequence
<220> FEATURE:
<223> OTHER INFORMATION: Description of Artificial Sequence: a sequence
      of binding region
```

```
<400> SEQUENCE: 2
gcugcuacaa g                                                              11

<210> SEQ ID NO 3
<211> LENGTH: 42
<212> TYPE: RNA
<213> ORGANISM: Artificial Sequence
<220> FEATURE:
<223> OTHER INFORMATION: Description of Artificial Sequence: a sequence
      of RNA probe No.5

<400> SEQUENCE: 3
ugguggugcu cuacaaguac cgcugcuaca aggugaggcc cu                            42

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: a sequence
      of RNA probe No.7

<400> SEQUENCE: 4
gcucuacaag gcugcuacaa g                                                  21

<210> SEQ ID NO 5
<211> LENGTH: 19
<212> TYPE: RNA
<213> ORGANISM: Artificial Sequence
<220> FEATURE:
<223> OTHER INFORMATION: Description of Artificial Sequence: a sequence
      of RNA probe No.9

<400> SEQUENCE: 5
ugguggugcu cuacaagua                                                     19

<210> SEQ ID NO 6
<211> LENGTH: 25
<212> TYPE: RNA
<213> ORGANISM: Artificial Sequence
<220> FEATURE:
<223> OTHER INFORMATION: Description of Artificial Sequence: a sequence
      of RNA probe No.10

<400> SEQUENCE: 6
gcucuacaag uaccgcugcu acaag                                              25

<210> SEQ ID NO 7
<211> LENGTH: 23
<212> TYPE: RNA
<213> ORGANISM: Artificial Sequence
<220> FEATURE:
<223> OTHER INFORMATION: Description of Artificial Sequence: a sequence
      of RNA probe No.11

<400> SEQUENCE: 7
ccgcugcuac aaggugaggc ccu                                                23

<210> SEQ ID NO 8
<211> LENGTH: 25
<212> TYPE: RNA
<213> ORGANISM: Artificial Sequence
<220> FEATURE:
<223> OTHER INFORMATION: Description of Artificial Sequence: a sequence
      of RNA probe No.8
```

```
<400> SEQUENCE: 8
gcucuaaaag uaccgcugcu aaaag                                    25

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: a sequence
      for primer ps251

<400> SEQUENCE: 9
attcagacct ctctgcggcc                                          20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: a sequence
      of primer ps231

<400> SEQUENCE: 10
aagcgggagc caaagtctgg                                          20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: a seqeunce
      for primer ps252

<400> SEQUENCE: 11
gttcgtggtg cttccagagg                                          20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: a sequence
      of primer ps233

<400> SEQUENCE: 12
ggaccactct gggaggtaca                                          20

<210> SEQ ID NO 13
<211> LENGTH: 60
<212> TYPE: DNA
<213> ORGANISM: Artificial Sequence
<220> FEATURE:
<223> OTHER INFORMATION: Description of Artificial Sequence: a sequence
      of DNA probe No.1

<400> SEQUENCE: 13
tctggatcct gccttctccc tcagcatcta cacgacattc actgaggaca cgaattcaga    60

<210> SEQ ID NO 14
<211> LENGTH: 60
<212> TYPE: DNA
<213> ORGANISM: Artificial Sequence
<220> FEATURE:
<223> OTHER INFORMATION: Description of Artificial Sequence: a sequence
      of DNA probe No.2
```

```
<400> SEQUENCE: 14
tctggatcct gaggacacac cctcggtggg ccagcgcctc ctcaactccg tgaattcaga      60

<210> SEQ ID NO 15
<211> LENGTH: 60
<212> TYPE: DNA
<213> ORGANISM: Artificial Sequence
<220> FEATURE:
<223> OTHER INFORMATION: Description of Artificial Sequence: a sequence
      of DNA probe No.3

<400> SEQUENCE: 15
tctggatccc aactccgtgc tgaacaccct catcatgatc agcgtcatcg tgaattcaga      60

<210> SEQ ID NO 16
<211> LENGTH: 60
<212> TYPE: DNA
<213> ORGANISM: Artificial Sequence
<220> FEATURE:
<223> OTHER INFORMATION: Description of Artificial Sequence: a sequence
      of DNA probe No.4

<400> SEQUENCE: 16
ctcggatcct gatcagcgtc atcgtggtta tgaccatctt cttggtggtg cgaattcgag      60

<210> SEQ ID NO 17
<211> LENGTH: 60
<212> TYPE: DNA
<213> ORGANISM: Artificial Sequence
<220> FEATURE:
<223> OTHER INFORMATION: Description of Artificial Sequence: a sequence
      of DNA probe No.5

<400> SEQUENCE: 17
tctggatcct ggtggtgctc tacaagtacc gctgctacaa ggtgaggccc tgaattcaga      60

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: a sequence
      of DNA probe No.6

<400> SEQUENCE: 18
gatccgacca tcttcttggt ggtg                                            24

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: a sequence
      of DNA probe No.7

<400> SEQUENCE: 19
gatccgctct acaaggctgc tacaagg                                         27

<210> SEQ ID NO 20
<211> LENGTH: 31
<212> TYPE: DNA
<213> ORGANISM: Artificial Sequence
<220> FEATURE:
<223> OTHER INFORMATION: Description of Artificial Sequence: a sequence
      of DNA probe No.8
```

```
<400> SEQUENCE: 20
gatccgctct aaaagtaccg ctgctaaaag g                                      31

<210> SEQ ID NO 21
<211> LENGTH: 37
<212> TYPE: DNA
<213> ORGANISM: Artificial Sequence
<220> FEATURE:
<223> OTHER INFORMATION: Description of Artificial Sequence: a sequence
      of DNA probe No.9

<400> SEQUENCE: 21
tctggatcct ggtggtgctc tacaagtaga attcaga                                37

<210> SEQ ID NO 22
<211> LENGTH: 43
<212> TYPE: DNA
<213> ORGANISM: Artificial Sequence
<220> FEATURE:
<223> OTHER INFORMATION: Description of Artificial Sequence: a sequence
      of DNA probe No.10

<400> SEQUENCE: 22
tctggatccg ctctacaagt accgctgcta caaggaattc aga                         43

<210> SEQ ID NO 23
<211> LENGTH: 41
<212> TYPE: DNA
<213> ORGANISM: Artificial Sequence
<220> FEATURE:
<223> OTHER INFORMATION: Description of Artificial Sequence: a sequence
      of DNA probe No.11

<400> SEQUENCE: 23
tctggatccc cgctgctaca aggtgaggcc ctgaattcag a                           41

<210> SEQ ID NO 24
<211> LENGTH: 49
<212> TYPE: RNA
<213> ORGANISM: Artificial Sequence
<220> FEATURE:
<223> OTHER INFORMATION: Description of Artificial Sequence: a sequence
      of 5'-amino-2'-O-methyl oligo RNA

<400> SEQUENCE: 24
aucuucuugg uggugcucua caaguaccgc ugcuacaagg ugaggcccu                   49

<210> SEQ ID NO 25
<211> LENGTH: 18
<212> TYPE: RNA
<213> ORGANISM: Artificial Sequence
<220> FEATURE:
<223> OTHER INFORMATION: Description of Artificial Sequence: a sequence
      of RNA probe No.6

<400> SEQUENCE: 25
gaccaucuuc uugguggu                                                     18

<210> SEQ ID NO 26
<211> LENGTH: 72
<212> TYPE: RNA
<213> ORGANISM: Artificial Sequence
<220> FEATURE:
<223> OTHER INFORMATION: Description of Artificial Sequence: a sequence
      of RNA probe No.12
```

-continued

```
<400> SEQUENCE: 26
ugguggugcu cuacaaguac cgcugcuaca aggugaggcc cuggcccugc ccuccagcca      60
cgcuucucuc cg                                                         72

<210> SEQ ID NO 27
<211> LENGTH: 25
<212> TYPE: RNA
<213> ORGANISM: Artificial Sequence
<220> FEATURE:
<223> OTHER INFORMATION: Description of Artificial Sequence: a sequence
      of 2'-O-methyl oligo RNA corresponding to a sequence of HMG-I
      protein binding region which is present in SEQ ID NO: 24

<400> SEQUENCE: 27
gcucuacaag uaccgcugcu acaag                                           25

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: a sequence
      of synthesized DNA containing HMG-I recognition motif

<400> SEQUENCE: 28
ggttcattct gcggtatggt tatctg                                          26

<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence: a sequence
      of synthesized DNA containing HMG-I recognition motif

<400> SEQUENCE: 29
atctgtaatt ccatggtggc tactggaact a                                    31

<210> SEQ ID NO 30
<211> LENGTH: 31
<212> TYPE: DNA
<213> ORGANISM: Artificial Sequence
<220> FEATURE:
<223> OTHER INFORMATION: Description of Artificial Sequence: a sequence
      of synthesized DNA containing HMG-I recognition motif

<400> SEQUENCE: 30
gtggaggctg ccgcgagtta tcacagtata g                                    31

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: a sequence
      of synthesized DNA containing HMG-I recognition motif

<400> SEQUENCE: 31
acctaggtta ttctgcggta tggttatctg                                      30

<210> SEQ ID NO 32
<211> LENGTH: 30
<212> TYPE: DNA
<213> ORGANISM: Artificial Sequence
```

```
<220> FEATURE:
<223> OTHER INFORMATION: Description of Artificial Sequence: a sequence
      of synthesized DNA containing HMG-I recognition motif

<400> SEQUENCE: 32
gggtgcctag ctccggaaca tggttattga                                    30

<210> SEQ ID NO 33
<211> LENGTH: 31
<212> TYPE: DNA
<213> ORGANISM: Artificial Sequence
<220> FEATURE:
<223> OTHER INFORMATION: Description of Artificial Sequence: a sequence
      of synthesized DNA containing HMG-I recognition motif

<400> SEQUENCE: 33
cgttctcttt cggaaacggt ttttgagcac g                                  31

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: a sequence
      of synthesized DNA containing HMG-I recognition motif

<400> SEQUENCE: 34
tgaggcatga aggtaattac tgcatattga                                    30

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: a sequence
      of synthesized DNA containing HMG-I recognition motif

<400> SEQUENCE: 35
ggccgcgtgt agatattggg atttggtgtg                                    30

<210> SEQ ID NO 36
<211> LENGTH: 28
<212> TYPE: DNA
<213> ORGANISM: Artificial Sequence
<220> FEATURE:
<223> OTHER INFORMATION: Description of Artificial Sequence: a sequence
      of synthesized DNA containing HMG-I recognition motif

<400> SEQUENCE: 36
cgttctcttt cggaaatttt tgagcacg                                      28

<210> SEQ ID NO 37
<211> LENGTH: 31
<212> TYPE: DNA
<213> ORGANISM: Artificial Sequence
<220> FEATURE:
<223> OTHER INFORMATION: Description of Artificial Sequence: a sequence
      of synthesized DNA containing HMG-I recognition motif

<400> SEQUENCE: 37
tgaccaagta aatccgtccc tcactagtga a                                  31

<210> SEQ ID NO 38
<211> LENGTH: 31
<212> TYPE: DNA
<213> ORGANISM: Artificial Sequence
```

```
<220> FEATURE:
<223> OTHER INFORMATION: Description of Artificial Sequence: a sequence
      of synthesized DNA containing HMG-I recognition motif

<400> SEQUENCE: 38
gccatgtttt tagataattg tgcttaggcg t                                      31

<210> SEQ ID NO 39
<211> LENGTH: 31
<212> TYPE: DNA
<213> ORGANISM: Artificial Sequence
<220> FEATURE:
<223> OTHER INFORMATION: Description of Artificial Sequence: a sequence
      of synthesized DNA containing HMG-I recognition motif

<400> SEQUENCE: 39
tctgaggcat gaaggtaatt actgcatcat t                                      31

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: a sequence
      of synthesized DNA containing HMG-I recognition motif

<400> SEQUENCE: 40
tatccagtgg ataattcccc aatgttatct                                        30

<210> SEQ ID NO 41
<211> LENGTH: 31
<212> TYPE: DNA
<213> ORGANISM: Artificial Sequence
<220> FEATURE:
<223> OTHER INFORMATION: Description of Artificial Sequence: a sequence
      of synthesized DNA containing HMG-I recognition motif

<400> SEQUENCE: 41
cgttccgacc aatgggttcg gataatacgt t                                      31

<210> SEQ ID NO 42
<211> LENGTH: 31
<212> TYPE: DNA
<213> ORGANISM: Artificial Sequence
<220> FEATURE:
<223> OTHER INFORMATION: Description of Artificial Sequence: a sequence
      of synthesized DNA containing HMG-I recognition motif

<400> SEQUENCE: 42
cttctgcggt ataaggtggg ttggtgtgct c                                      31

<210> SEQ ID NO 43
<211> LENGTH: 31
<212> TYPE: DNA
<213> ORGANISM: Artificial Sequence
<220> FEATURE:
<223> OTHER INFORMATION: Description of Artificial Sequence: a sequence
      of synthesized DNA containing HMG-I recognition motif

<400> SEQUENCE: 43
gaggtgtcag gcgacaccta aaaattcacg c                                      31

<210> SEQ ID NO 44
<211> LENGTH: 32
<212> TYPE: DNA
<213> ORGANISM: Artificial Sequence
```

-continued

```
<220> FEATURE:
<223> OTHER INFORMATION: Description of Artificial Sequence: a sequence
      of synthesized DNA containing HMG-I recognition motif

<400> SEQUENCE: 44
atatcctgcc aaaaatttgt tctcggggct ga                                32

<210> SEQ ID NO 45
<211> LENGTH: 31
<212> TYPE: DNA
<213> ORGANISM: Artificial Sequence
<220> FEATURE:
<223> OTHER INFORMATION: Description of Artificial Sequence: a sequence
      of synthesized DNA containing HMG-I recognition motif

<400> SEQUENCE: 45
tgtttcgcgt aaagtattac gttgctcttt t                                 31

<210> SEQ ID NO 46
<211> LENGTH: 31
<212> TYPE: DNA
<213> ORGANISM: Artificial Sequence
<220> FEATURE:
<223> OTHER INFORMATION: Description of Artificial Sequence: a sequence
      of synthesized DNA containing HMG-I recognition motif

<400> SEQUENCE: 46
gtcgggcctg tattttggtt gctattttga a                                 31

<210> SEQ ID NO 47
<211> LENGTH: 31
<212> TYPE: DNA
<213> ORGANISM: Artificial Sequence
<220> FEATURE:
<223> OTHER INFORMATION: Description of Artificial Sequence: a sequence
      of synthesized DNA containing HMG-I recognition motif

<400> SEQUENCE: 47
gcgagtcggg cctgtatttt ggttgctatt t                                 31

<210> SEQ ID NO 48
<211> LENGTH: 32
<212> TYPE: DNA
<213> ORGANISM: Artificial Sequence
<220> FEATURE:
<223> OTHER INFORMATION: Description of Artificial Sequence: a sequence
      of synthesized DNA containing HMG-I recognition motif

<400> SEQUENCE: 48
ttgaattagg gtgctatatt tttgcatttt ga                                32

<210> SEQ ID NO 49
<211> LENGTH: 31
<212> TYPE: DNA
<213> ORGANISM: Artificial Sequence
<220> FEATURE:
<223> OTHER INFORMATION: Description of Artificial Sequence: a sequence
      of synthesized DNA containing HMG-I recognition motif

<400> SEQUENCE: 49
gtcgggcctg tattttggtt gctattttga a                                 31

<210> SEQ ID NO 50
<211> LENGTH: 31
<212> TYPE: DNA
<213> ORGANISM: Artificial Sequence
```

```
<220> FEATURE:
<223> OTHER INFORMATION: Description of Artificial Sequence: a sequence
      of synthesized DNA containing HMG-I recognition motif

<400> SEQUENCE: 50
gcgagtcggg cctgtatttt ggttgctatt t                              31

<210> SEQ ID NO 51
<211> LENGTH: 32
<212> TYPE: DNA
<213> ORGANISM: Artificial Sequence
<220> FEATURE:
<223> OTHER INFORMATION: Description of Artificial Sequence: a sequence
      of synthesized DNA containing HMG-I recognition motif

<400> SEQUENCE: 51
ccactttgaa ttagggtgct atatttttgc at                             32

<210> SEQ ID NO 52
<211> LENGTH: 31
<212> TYPE: DNA
<213> ORGANISM: Artificial Sequence
<220> FEATURE:
<223> OTHER INFORMATION: Description of Artificial Sequence: a sequence
      of synthesized DNA containing HMG-I recognition motif

<400> SEQUENCE: 52
gtggataaat tccccaatgt tatcttatga a                              31

<210> SEQ ID NO 53
<211> LENGTH: 32
<212> TYPE: DNA
<213> ORGANISM: Artificial Sequence
<220> FEATURE:
<223> OTHER INFORMATION: Description of Artificial Sequence: a sequence
      of synthesized DNA containing HMG-I recognition motif

<400> SEQUENCE: 53
ctttgaatta gggtgctata ttttttgcat tt                             32

<210> SEQ ID NO 54
<211> LENGTH: 35
<212> TYPE: DNA
<213> ORGANISM: Artificial Sequence
<220> FEATURE:
<223> OTHER INFORMATION: Description of Artificial Sequence: a sequence
      of synthesized DNA containing HMG-I recognition motif

<400> SEQUENCE: 54
cgtgtttcgc cagaaccgca ctagagcaat ttgaa                          35

<210> SEQ ID NO 55
<211> LENGTH: 33
<212> TYPE: DNA
<213> ORGANISM: Artificial Sequence
<220> FEATURE:
<223> OTHER INFORMATION: Description of Artificial Sequence: a sequence
      of synthesized DNA containing HMG-I recognition motif

<400> SEQUENCE: 55
ctttgaatta gggtgctata tggtttgcat ttt                            33

<210> SEQ ID NO 56
<211> LENGTH: 31
<212> TYPE: DNA
<213> ORGANISM: Artificial Sequence
```

-continued

```
<220> FEATURE:
<223> OTHER INFORMATION: Description of Artificial Sequence: a sequence
      of synthesized DNA containing HMG-I recognition motif

<400> SEQUENCE: 56
gtggataaat tccccaatgt tatcttatga a                                        31

<210> SEQ ID NO 57
<211> LENGTH: 31
<212> TYPE: DNA
<213> ORGANISM: Artificial Sequence
<220> FEATURE:
<223> OTHER INFORMATION: Description of Artificial Sequence: a sequence
      of synthesized DNA containing HMG-I recognition motif

<400> SEQUENCE: 57
ggtgccgata cgtaactcac cgcattcttg g                                        31

<210> SEQ ID NO 58
<211> LENGTH: 31
<212> TYPE: DNA
<213> ORGANISM: Artificial Sequence
<220> FEATURE:
<223> OTHER INFORMATION: Description of Artificial Sequence: a sequence
      of synthesized DNA containing HMG-I recognition motif

<400> SEQUENCE: 58
cgttccgacc aatgggttcg gataatacgt t                                        31

<210> SEQ ID NO 59
<211> LENGTH: 31
<212> TYPE: DNA
<213> ORGANISM: Artificial Sequence
<220> FEATURE:
<223> OTHER INFORMATION: Description of Artificial Sequence: a sequence
      of synthesized DNA containing HMG-I recognition motif

<400> SEQUENCE: 59
ggtgccgata cgtaactcac cgcattttgg c                                        31

<210> SEQ ID NO 60
<211> LENGTH: 31
<212> TYPE: DNA
<213> ORGANISM: Artificial Sequence
<220> FEATURE:
<223> OTHER INFORMATION: Description of Artificial Sequence: a sequence
      of synthesized DNA containing HMG-I recognition motif

<400> SEQUENCE: 60
ggtgccgata cgtaatcacc gcattcttgg c                                        31

<210> SEQ ID NO 61
<211> LENGTH: 31
<212> TYPE: DNA
<213> ORGANISM: Artificial Sequence
<220> FEATURE:
<223> OTHER INFORMATION: Description of Artificial Sequence: a sequence
      of synthesized DNA containing HMG-I recognition motif

<400> SEQUENCE: 61
cactttgaat tagggtgcta tatgttttgc a                                        31

<210> SEQ ID NO 62
<211> LENGTH: 31
<212> TYPE: DNA
<213> ORGANISM: Artificial Sequence
```

```
<220> FEATURE:
<223> OTHER INFORMATION: Description of Artificial Sequence: a sequence
      of synthesized DNA containing HMG-I recognition motif

<400> SEQUENCE: 62
ttgaattagg gtgctatatg ttttgcattt t                              31

<210> SEQ ID NO 63
<211> LENGTH: 31
<212> TYPE: DNA
<213> ORGANISM: Artificial Sequence
<220> FEATURE:
<223> OTHER INFORMATION: Description of Artificial Sequence: a sequence
      of synthesized DNA containing HMG-I recognition motif

<400> SEQUENCE: 63
cgttctcttt cggaaacggt ttttgagcac g                              31

<210> SEQ ID NO 64
<211> LENGTH: 31
<212> TYPE: DNA
<213> ORGANISM: Artificial Sequence
<220> FEATURE:
<223> OTHER INFORMATION: Description of Artificial Sequence: a sequence
      of synthesized DNA containing HMG-I recognition motif

<400> SEQUENCE: 64
aggttcgtgc acccggacca cagttttttc a                              31

<210> SEQ ID NO 65
<211> LENGTH: 70
<212> TYPE: DNA
<213> ORGANISM: Artificial Sequence
<220> FEATURE:
<223> OTHER INFORMATION: Description of Artificial Sequence: a sequence
      of synthesized DNA used in in vitro DNA selection assay
<220> FEATURE:
<223> OTHER INFORMATION: n is g or a or t or c

<400> SEQUENCE: 65
ggtgatcaga ttctgatcca nnnnnnnnnn nnnnnnnnnn nnnnnnnnnn ntgaagcttg    60
gatccgtcgc                                                           70

<210> SEQ ID NO 66
<211> LENGTH: 14
<212> TYPE: DNA
<213> ORGANISM: Artificial Sequence
<220> FEATURE:
<223> OTHER INFORMATION: Description of Artificial Sequence: a sequence
      of synthesized DNA containing HMG-I recognition motif

<400> SEQUENCE: 66
gcgrgwwatt tcgc                                                 14

<210> SEQ ID NO 67
<211> LENGTH: 39
<212> TYPE: DNA
<213> ORGANISM: Artificial Sequence
<220> FEATURE:
<223> OTHER INFORMATION: Description of Artificial Sequence: a sequence
      of primer for the use for in vitro DNA selection assay

<400> SEQUENCE: 67
gtaatacgac tcactatagg ggtgatcagat tctgatcca                     39
```

```
<210> SEQ ID NO 68
<211> LENGTH: 19
<212> TYPE: DNA
<213> ORGANISM: Artificial Sequence
<220> FEATURE:
<223> OTHER INFORMATION: Description of Artificial Sequence: a sequence
      of primer for the use for in vitro DNA selection assay

<400> SEQUENCE: 68
gcgacggatc caagcttca                                                19
```

The invention claimed is:

1. A method for screening an inhibitor for binding between exon 5 of presenilin-2 gene and high mobility group box 1 (HMG-I) protein, comprising:
   detecting the presence or absence of a substance to be tested, a binding between HMG-I protein and
   a nucleic acid capable of binding to HMG-I protein wherein said nucleic acid consists of the sequence of SEQ ID NO: 4,
   or determining a binding strength of the binding, wherein the following I) or II):
   I) the binding between the nucleic acid and the HMG-I protein is not detected in the presence of the substance to be tested, or
   II) a binding strength of binding between the nucleic acid and the HMG-I protein in the presence of the substance to be tested is smaller than a binding strength of binding between the nucleic acid and the HMG-I protein in the absence of the substance to be tested
   Is used as an index, thereby showing that the substance to be tested is an inhibitor for binding between exon 5 of presenilin-2 gene and HMG-I protein.

2. The screening method according to claim 1, wherein the method comprises:
   (A) contacting said nucleic acid with HMG-I protein in the presence of the substance to be tested; and
   (B) detecting binding between the nucleic acid and the HMG-I protein.

3. The screening method according to claim 1, wherein the method comprises:
   (A) contacting said nucleic acid with HMG-I protein under each condition of the presence and absence of the substance to be tested; and
   (B) determining a binding strength of binding between the nucleic acid and the HMG-I protein in the presence of a substance to be tested and a binding strength of binding between the nucleic acid and the HMG-I protein in the absence of a substance to be tested.

4. An isolated nucleic acid capable of binding to high mobility group box 1 (HMG-I) protein, wherein the nucleic acid consists of the sequence of SEQ ID NO:4.

5. An isolated nucleic acid molecule consisting of the full complement of the sequence of SEQ ID NO:4.

* * * * *

UNITED STATES PATENT AND TRADEMARK OFFICE
CERTIFICATE OF CORRECTION

PATENT NO. : 7,364,847 B2  
APPLICATION NO. : 10/482115  
DATED : April 29, 2008  
INVENTOR(S) : Masaya Tohyama et al.

It is certified that error appears in the above-identified patent and that said Letters Patent is hereby corrected as shown below:

Title Pg. Item (73) Assignee: Japan Science and Tehcnology Agency" should read -- Assignee: Japan Science and Technology Agency --

Signed and Sealed this

Second Day of September, 2008

JON W. DUDAS  
*Director of the United States Patent and Trademark Office*